United States Patent [19]

Akhavan-Tafti et al.

[11] Patent Number: 5,593,845

[45] Date of Patent: *Jan. 14, 1997

[54] ARYL N-ALKYLACRIDANCARBOXYLATE DERIVATIVES USEFUL FOR CHEMILUMINESCENT DETECTION

[75] Inventors: Hashem Akhavan-Tafti, Sterling Heights; Renuka DeSilva, Northville; Zahra Arghavani, Sterling Heights; Barry A. Schoenfelner, Livonia, all of Mich.

[73] Assignee: Lumigen, Inc., Southfield, Mich.

[*] Notice: The portion of the term of this patent subsequent to May 17, 2013, has been disclaimed.

[21] Appl. No.: 205,093

[22] Filed: Mar. 2, 1994

Related U.S. Application Data

[63] Continuation-in-part of Ser. No. 61,810, May 17, 1993.

[51] Int. Cl.$^6$ ............................................ G01N 33/535
[52] U.S. Cl. ................... 435/7.9; 435/7.1; 435/7.92; 435/28; 435/968; 252/700
[58] Field of Search ..................... 435/7.1, 7.9, 7.92, 435/28, 968; 252/700; 546/102

[56] References Cited

U.S. PATENT DOCUMENTS

| | | | |
|---|---|---|---|
| 4,927,769 | 5/1990 | Chang | 436/518 |
| 5,145,772 | 9/1992 | Voyta | 435/4 |
| 5,171,668 | 12/1992 | Sugiyama | 435/28 |
| 5,206,149 | 4/1993 | Oyama | 435/28 |
| 5,283,334 | 2/1994 | McCapra | 546/104 |

OTHER PUBLICATIONS

Steenken, S., Photochem. Photobiol., 11, 279–283 (1970).
Hapiot, P., J. Moiroux, J. M. Saveant, J. Am. Chem. Soc., 112 (4), 1337–43 (1990).
Koper, N. W., S. A. Jonker, J. W. Verhoeven, Recl. Trav. Chim. Pays–Bas, 104(11), 296–302 (1985).
Sinha, A., T. C. Bruice, J. Am. Chem. Soc., 106(23), 7291–2 (1984).
Colter, A. K., P. Plank, J. P. Bergsma, R. Lahti, A. A. Quesnel, A. G. Parsons, Can. J. Chem., 62(9), 1780–4 (1984).
Chupakhin, O. N., I. M. Sosonkin, A. I. Matern, G. N. Strogov, Dokl. Akad. Nauk SSSR, 250(4), 875–7 (1980).
Knappe, W. R., J. Pharm. Sci., 67(3), 318–20 (1978).
Digenis, G. A., S. Shakshir, M. A. Miyamoto, H. B. Kostenbauer, J. Pharm. Sci., 65(2), 247–51 (1976).
McCapra, F., Accts. Chem. Res., 9(6), 201–8 (1976).
McCapra, R., M. Roth, D. Hysert, K. A. Zaklika in Chemiluminescence and Bioluminescence, Plenum Press, New York, pp. 313–321 (1973).
McCapra, F., Prog. Org. Chem., 8, 231–277 (1971).
McCapra, F., Pure Appl. Chem., 24, 611–629 (1970).
Kinkel, T., H. Lubbers, E. Schmidt, P. Molz, H. J. Skripczyk, J. Biolumin. Chemilumin., 4, 136–139 (1989).
Zomer, G., J. F. C. Stavenuiter, Anal. Chim. Acta, 227, 11–19 (1989).
Law, S.–J., T. Miller, U. Piran, C. Klukas, S. Chang, J. Unger, J. Biolumin. Chemilumin., 4, 88–98 (1989).
Ii, M., H. Yoshida, Y. Aramaki, H. Masuya, T. Hada, M. Terada, M. Hatanaka, Y. Ichimori Biochem, Biophys. Res. Comm., 193(2), 540–5 (1993).
Thorpe, G., L. Kricka, in Biolum. and Chemilumin., New Perspectives, J. Scholmerich, et al., Eds., pp. 199–208 (1987).
Lumdin, A., L. Hallander, in Biolumin. and Chemi–lumin., New Perspectives, J. Scholmerich, et al. Eds., pp. 555–558 (1987).
Vlasenko, S., A. Arefyev, A. Klimov, B. Kim, E. Gorovits, A. Osipov, E. Gavrilova, A. Yegorov, J. Biolumin. Chemilumin. 4,164–176 (1989).
Thorpe, G. H., et al., Clin. Chem., 31, 1335 (1985).
Matthews, J. A., et al., Anal. Biochem., 151,205 (1985).
Kricka, L. J., et al., Arch. Biochem. Biophys., 217, 674 (1983).
Goto, T., et al., Tetrahedron. Lett., 4299 (1969).
Sasamoto, K., et al., Chem. Pharm. Bull. 39(2) 411–6 (1991).
Stott, R. A. W., et al, Biolumin. and Chemilumin. J. Scholmerich, et al., Eds., pp. 237–240 (1987).
Advanced Organic Chemistry, F. A. Carey and R. J. Sundberg, Plenum Press, p. 145 (1977).
Walsh, P. S., Nucleic Acids Research, vol. 20, No. 19 5061–5065 (1992).

*Primary Examiner*—Lora M. Green
*Attorney, Agent, or Firm*—Ian C. McLeod

[57] ABSTRACT

Acridans which are reactable with a peroxidase and peroxide. The acridans are characterized by having an aromatic leaving group ArO which is a di- or polyhalosubstituted phenoxy group. The compounds are useful in assays where one member of a binding pair is linked to the peroxidase and for detecting the peroxidase. The method can also be used to detect hydrogen peroxide.

38 Claims, 14 Drawing Sheets

1 2 3 4 5

1 2 3 4 5

1 2 3 4 5

1 2 3 4 5

1 2 3 4 5

1 2 3 4 5

1 2 1 2

ARYL N-ALKYLACRIDANCARBOXYLATE DERIVATIVES USEFUL FOR CHEMILUMINESCENT DETECTION

CROSS REFERENCE TO RELATED APPLICATION

This application is a continuation-in-part of applicant's co-pending application Ser. No. 08/061,810 filed on May 17, 1993.

BACKGROUND OF THE INVENTION

1. Field of the Invention

This invention relates to chemiluminescent N-alkylacridancarboxylate derivatives which allow the production of light (chemiluminescence) from the acridan by reaction with a peroxide and a peroxidase. This invention also relates to an improved method of generating light chemically (chemiluminescence) by the action of a peroxidase enzyme and an oxidant such as hydrogen peroxide with a group of N-alkylacridancarboxylate derivatives. The invention also relates to an improved method of enhancing the amount of chemiluminescence produced from this process by the use of specific substances. The invention also relates to the use of this method to detect the peroxidase enzyme. The invention also relates to the use of this method to detect hydrogen peroxide. Further, the invention relates to the use of the method to detect and quantitate various biological molecules. For example, the method may be used to detect haptens, antigens and antibodies by the technique of immunoassay, proteins by Western blotting, DNA and RNA by Southern and Northern blotting, respectively. The method may also be used to detect DNA in DNA sequencing applications. The method may additionally be used to detect enzymes which generate hydrogen peroxide such as glucose oxidase, glucose-6-phosphate dehydrogenase, galactose oxidase and the like as are generally known in the art.

2. Description of Related Art

The detection and quantitation of biological molecules has been accomplished historically with excellent sensitivity by the use of radiolabeled reporter molecules. Recently numerous non-radioactive methods have been developed to avoid the hazards and inconvenience posed by these materials. Methods based on enzyme-linked analytes offer the best sensitivity since the ability to catalytically turn over substrate to produce a detectable change achieves an amplification. Substrates which generate color, fluorescence or chemiluminescence have been developed, the latter achieving the best sensitivity.

Further increases in assay sensitivity will expand the range of utility of chemiluminescence-based methods by permitting the detection of analytes present in smaller quantities or reducing the amount of time and/or reagents required to perform the assay. A way to increase the speed and sensitivity of detection in an enzymatic chemiluminescent assay is through the use of substrates which generate light with a higher efficiency or for a greater length of time.

Among the enzymes used in enzyme-linked detection methods such as immunoassays, detection of oligonucleotides and nucleic acid hybridization techniques, the most extensively used to date has been horseradish peroxidase. Chemiluminescent reagents known in the art do not permit full advantage to be taken of the beneficial properties of this enzyme in analysis mainly due to sensitivity limitations. A reagent which permits the detection of lower amounts of enzyme is needed to enable the use of peroxidase conjugates in applications requiring ultrasensitive detection. Specifically, reagents are required which generate higher levels of chemiluminescence without an accompanying increase in the background or non-specific chemiluminescence. The increased chemiluminescence may be accomplished via either a higher maximum intensity or a longer duration than compounds known in the art.

a. Oxidation of acridan. Oxidation of acridan by benzoyl peroxide in aqueous solution produced chemiluminescence with very low efficiency ($\phi_{CL}=3\times10^{-7}$) and a mixture of products including acridine (S. Steenken, Photochem. Photobiol., 11, 279–283 (1970)). N-Methylacridan is oxidized electrochemically to N-methylacridinium ion (P. Hapiot, J. Moiroux, J. M. Saveant, J. Am. Chem. Soc., 112(4), 1337–43 (1990); N. W. Koper, S. A. Jonker, J. W. Verhoeven, Recl. Trav. Chim. Pays-Bas, 104(11), 296–302 (1985)). Chemical oxidation of N-alkylacridan compounds has been performed with ferricyanide ion (A. Sinha, T. C. Bruice, J. Am. Chem. Soc., 106(23), 7291–2 (1984)), certain quinones (A. K. Colter, P. Plank, J. P. Bergsma, R. Lahti, A. A. Quesnel, A. G. Parsons, Can. J. Chem., 62(9), 1780–4 (1984)) and lithium nitrite (O. N. Chupakhin, I. M. Sosonkin, A. I. Matern, G. N. Strogov, Dokl. Akad. Nauk SSSR, 250(4), 875–7 (1980)). Oxidation of an N-alkylacridan derivative has been performed photochemically with or without a flavin compound as co-oxidant (W. R. Knappe, J. Pharm. Sci., 67(3), 318–20 (1978); G. A. Digenis, S. Shakshir, M. A. Miyamoto, H. B. Kostenbauer, J. Pharm. Sci., 65(2), 247–51 (1976)).

Aryl and alkyl esters of 10-methylacridan-9-carboxylic acid undergo autoxidation to N-methylacridone in dipolar aprotic solvents under strongly basic conditions to produce chemiluminescence (F. McCapra, Accts. Chem. Res., 9(6), 201–8 (1976); F. McCapra, M. Roth, D. Hysert, K. A. Zaklika in Chemiluminescence and Bioluminescence, Plenum Press, New York, 1973, pp. 313–321; F. McCapra, Prog. Org. Chem., 8, 231–277 (1971); F. McCapra, Pure Appl. Chem., 24, 611–629 (1970); U.S. Pat. No. 5,283,334 to McCapra). Chemiluminescence quantum yields ranged from $10^{-5}$ to 0.1 and were found to increase as the pKa of the phenol or alcohol leaving group decreased. Quantum yields in aqueous solution were significantly lower due a competing non-luminescent decomposition of an intermediate. Addition of the cationic surfactant CTAB increased the apparent light yield 130-fold by preventing a competing dark reaction.

Applicants' co-pending application Ser. No. 08/061,810 discloses the first use of an enzyme to oxidize substituted and unsubstituted N-alkylacridancarboxylic acid derivatives to generate chemiluminescence. In the presence of a peroxidase enzyme and a peroxide, N-alkylacridancarboxylate derivatives are efficiently oxidized to produce the N-alkylacridone and blue chemiluminescence.

b. Chemiluminescent oxidation of acridinium esters. The chemiluminescent oxidation of aliphatic and aromatic esters of N-alkylacridinium carboxylic acid by $H_2O_2$ in alkaline solution is a well known reaction. The high chemiluminescence quantum yield approaching 0.1 has led to development of derivatives with pendant reactive groups for attachment to biological molecules. Numerous chemiluminescent immunoassays and oligonucleotide probe assays utilizing acridinium ester labels have been reported.

The use of acridinium esters (AE's), especially when labeled to a protein or oligonucleotide suffers from two disadvantages. The chief problem is limited hydrolytic stability. Acridinium ester conjugates decompose steadily at or slightly above room temperature. Depending on the substitution of the leaving group storage at −20° C. may be required for extended storage.

A second disadvantage of acridinium esters is the tendency to add nucleophiles such as water at the 9-position to spontaneously form a pseudo-base intermediate which is non-luminescent and decomposes in a pH-dependent manner in a dark process. In practice the pH of solutions containing acridinium esters must be first lowered to reverse pseudo-base formation and then raised in the presence of $H_2O_2$ to produce light.

Amides, thioesters and sulfonamides of N-alkylacridinium carboxylic acid have been shown to emit light when oxidized under these conditions (T. Kinkel, H. Lubbers, E. Schmidt, P. Molz, H. J. Skripczyk, J. Biolumin. Chemilumin., 4, 136–139, (1989), G. Zomer, J. F. C. Stavenuiter, Anal. Chim. Acta, 227, 11–19 (1989)). These modifications of the leaving group only partially improve the storage stability performance.

A more fundamental limitation to the use of acridinium esters as chemiluminescent labels lies in the fact that when used as direct labels, only up to at most about 10 molecules can be attached to a protein or oligonucleotide. Coupled with the quantum efficiency for producing a photon ($\leq 10\%$), an acridinium ester-labeled analyte can generate at most one photon of light. In contrast, enzyme-labeled analytes detected by a chemiluminescent reaction can potentially generate several orders of magnitude more light per analyte molecule detected by virtue of the catalytic action of the enzyme.

An attempt to increase the number of acridinium ester molecules associated with an analyte in an immunoassay was made by constructing an antibody-liposome conjugate wherein the liposome contained an unspecified number of AE's (S.-J. Law, T. Miller, U. Piran, C. Klukas, S. Chang, J. Unger, J. Biolumin. Chemilumin., 4, 88–98, (1989)). This method only produced a modest increase in signal over a comparable assay using directly labeled AE's.

c. Chemiluminescent Detection of Horseradish Peroxidase. Amino-substituted cyclic acylhydrazides such as luminol and isoluminol react with $H_2O_2$ and a peroxidase enzyme catalyst (such as horseradish peroxidase, HRP) under basic conditions with emission of light. This reaction has been used as the basis for analytical methods for the detection of $H_2O_2$ and for the peroxidase enzyme. An analog of luminol (8-amino-5-chloro-7-phenylpyrido[3,4-d]pyridazine-1,4 (2H, 3H)dione) has been used in an enhanced chemiluminescent assay with HRP (M. Ii, H. Yoshida, Y. Aramaki, H. Masuya, T. Hada, M. Terada, M. Hatanaka, Y. Ichimori, Biochem. Biophys. Res. Comm., 193(2), 540–5 (1993)). Application of this compound in an immunoassay led to a two-fold lowering of the detection limit compared to detection using luminol. Another chemiluminescent compound oxidized by a peroxidase enzyme and a peroxide is a hydroxy-substituted phthalhydrazide (Akhavan-Tafti co-pending U.S. patent application No. 965,231, filed Oct. 23, 1992). Applicant's co-pending application Ser. No. 08/061,810 filed on May 17, 1993 discloses chemiluminescent N-alkylacridancarboxylic acid esters and sulfonimides which produce light upon reaction with a peroxide and a peroxidase for use in detecting peroxidase enzymes and in assays.

Numerous enhancers have also been employed in conjunction with the use of luminol to increase the intensity and duration of light emitted. These include benzothiazole derivatives such as D-luciferin, various phenolic compounds such as p-iodophenol and p-phenylphenol and aromatic amines (G. Thorpe, L. Kricka, in Bioluminescence and Chemiluminescence, New Perspectives, J. Scholmerich, et al, Eds., pp. 199–208 (1987)). For the purposes of the present discussion phenolic compounds are taken to mean hydroxylic aromatic compounds which will also include compounds such as 2-naphthol and 6-bromo-2-naphthol which are known to enhance other peroxidase reactions in addition to the aforementioned substituted hydroxyphenyl compounds. Other compounds which function as enhancers of the chemiluminescent oxidation of amino-substituted cyclic acylhydrazides by a peroxidase include 4-(4-hydroxyphenyl) thiazole (M. Ii, H. Yoshida, Y. Aramaki, H. Masuya, T. Hada, M. Terada, M. Hatanaka, Y. Ichimori, Biochem. Biophys. Res. Comm., 193 (2) , 540–5 (1993)), a group of compounds disclosed in U.S. Pat. No. 5,171,668 to Sugiyama, 2-hydroxy-9-fluorenone, and a group of hydroxy-substituted benzoxazole derivatives as disclosed in U.S. Pat. No. 5,206,149 to Oyama. The mechanism of oxidation of cyclic acylhydrazides by the combination of a peroxide and a peroxidase enzyme is very complex and remains the subject of intense debate (A. Lundin, L. Hallander, in Bioluminescence and Chemiluminescence, New Perspectives, J. Scholmerich, et al, Eds., pp. 555–558 (1987)); S. Vlasenko, A Arefyev, A. Klimov, B. Kim, E. Gorovits, A. Osipov, E. Gavrilova, A. Yegorov, J. Biolumin. Chemilumin. 4, 164–176 (1989)). This difficulty has hampered the development of new chemiluminescent reactions catalyzed by peroxidases.

d. Assays using HRP. The enzyme horseradish peroxidase has found widespread use in enzyme immunoassays and DNA hybridization assays with chemiluminescent detection using luminol or isoluminol as substrate (G. H. Thorpe, L. J. Kricka, S. B. Mosely, T. P. Whitehead Clin. Chem., 31, 1335 (1985), J. A. Matthews, A. Batki, C. Hynds, L. J. Kricka, Anal. Biochem., 151,205, (1985), P. Walsh, J. Varlaro, R. Reynolds, Nuc. Acids Res. 20,(19) 5061–5065 (1992)). Commercially available kits for conjugation of HRP with enhanced luminol chemiluminescent detection are available. Chemiluminescent assays using a peroxidase enzyme known in the art are not able to detect the lowest levels of certain analytes such as the thyroid hormone TSH, mainly due to the inability to detect the enzyme at extremely low levels. A chemiluminescent reagent which permits the detection of lower amounts of enzyme is needed for such assays.

e. Chemiluminescence Enhancement by Surfactants. Enhancement of chemiluminescent reactions using polymeric and monomeric surfactants is known in the art. Enhancement may occur by affecting the outcome of one or more steps e.g. by increasing the fluorescence quantum yield of the emitter, by increasing the percentage of product molecules produced in the excited state, by increasing the fraction of molecules undergoing the chemiluminescent reaction through inhibition of competing side reactions (McCapra Accts. Chem. Res., 9(6), 201–8 (1976)) or by promoting the action of an enzyme catalyst. No clear or consistent pattern exists concerning the effect of polymeric and monomeric surfactants on chemiluminescent reactions. It is impossible to predict which surfactant compounds, if any, may enhance the chemiluminescence from a particular process and can only be determined by substantial experimentation.

U.S. Pat. No. 5,145,772 to Voyta discloses enhancement of enzymatically generated chemiluminescence from 1,2-dioxetanes in the presence of polymeric compounds. Certain cationic polymer compounds were effective chemiluminescence enhancers; nonionic polymeric compounds were generally ineffective and the lone anionic polymer, Example 45, significantly decreased light emission.

U.S. Pat. No. 4,927,769 to Chang discloses enhancement by surfactants of the chemical oxidation of acridinium esters with alkaline hydrogen peroxide. These acridinium ester compounds are discrete from compounds of the present invention in that they react without the use of enzymes. Several of the tested surfactants (see Table 2 therein) provide only marginal enhancement.

A report on the effect of surfactants on the firefly luciferin-luciferase reaction (L. J. Kricka, M. DeLuca, Arch. Biochem. Biophys., 217, 674 (1983)) discloses enhancement of the light yield with nonionic surfactants by affecting the enzyme reactivity; a cationic surfactant totally extinguished light emission by inhibiting the enzyme.

A paper (T. Goto, H. Fukatsu, Tetrahedron. Lett., 4299 (1969)) teaches chemiluminescence enhancement of the chemical oxidation of Cypridina luciferin in the presence of nonionic and cationic but not anionic surfactants even though the fluorescence quantum yield of the emitter was increased in all three types of surfactants.

A paper (K. Sasamoto, Y. Ohkura, Chem. Pharm. Bull, 39(2), 411–6 (1991)) discloses enhancement by a cationic surfactant of chemiluminescence from chemical oxidation of a dialkylaminobenzofuranyl-substituted cyclic diacylhydrazide. An anionic surfactant was ineffective at enhancing the chemiluminescence, while a nonionic surfactant diminished light production.

OBJECTS

It is therefore an object of the present invention to provide an improved method and N-alkylacridancarboxylate derivatives with superior properties for use in generating chemiluminescence by the action of a peroxidase enzyme for the detection of biological materials and compounds. It is also an object of the present invention to provide an improved method and kit using N-alkylacridancarboxylate derivatives in solution or on membranes for use in generating chemiluminescence by the action of a peroxidase enzyme for the detection of peroxidase enzymes and enzyme-conjugates. Additionally, it is an object of the present invention to provide an improved method and kit using N-alkylacridancarboxylate derivatives for use in generating chemiluminescence by the action of a peroxidase enzyme for use in nucleic acid assays in solution and on surfaces. Further, it is an object of the present invention to provide an improved method and kit using N-alkylacridancarboxylate derivatives for use in generating chemiluminescence by the action of a peroxidase enzyme for detection of proteins in Western blots and DNA in Southern blots and other DNA hybridization assays. Further, it is an object of the present invention to provide an improved method and kit using N-alkylacridancarboxylate derivatives for use in generating chemiluminescence by the action of a peroxidase enzyme for detection of haptens, proteins and antibodies in enzyme immunoassays.

BRIEF DESCRIPTION OF THE DRAWINGS

FIG. 1 shows the improved generation of light emission (in Relative Light Units, RLU) using 5a, a reagent of the present invention, under these conditions compared to the prior art compounds 4'-fluorophenyl 10-methylacridan-9-carboxylate and luminol.

FIG. 2 shows the improved generation of light emission using 5b, a reagent of the present invention, compared to the prior art compounds.

FIG. 3 shows the improved generation of light emission using 5c, a reagent of the present invention, compared to the prior art compounds.

FIG. 4 shows the improved generation of light emission using 5d, a reagent of the present invention, compared to the prior art compounds.

FIG. 5 shows the improved generation of light emission using 5e, a reagent of the present invention, compared to the prior art compounds.

FIG. 6 shows the improved generation of light emission using 5f, a reagent of the present invention, compared to the prior art compounds.

FIG. 7 shows the improved generation of light emission using 5h, a reagent of the present invention, compared to the prior art compounds.

DESCRIPTION OF THE PREFERRED EMBODIMENTS

Figure 1:
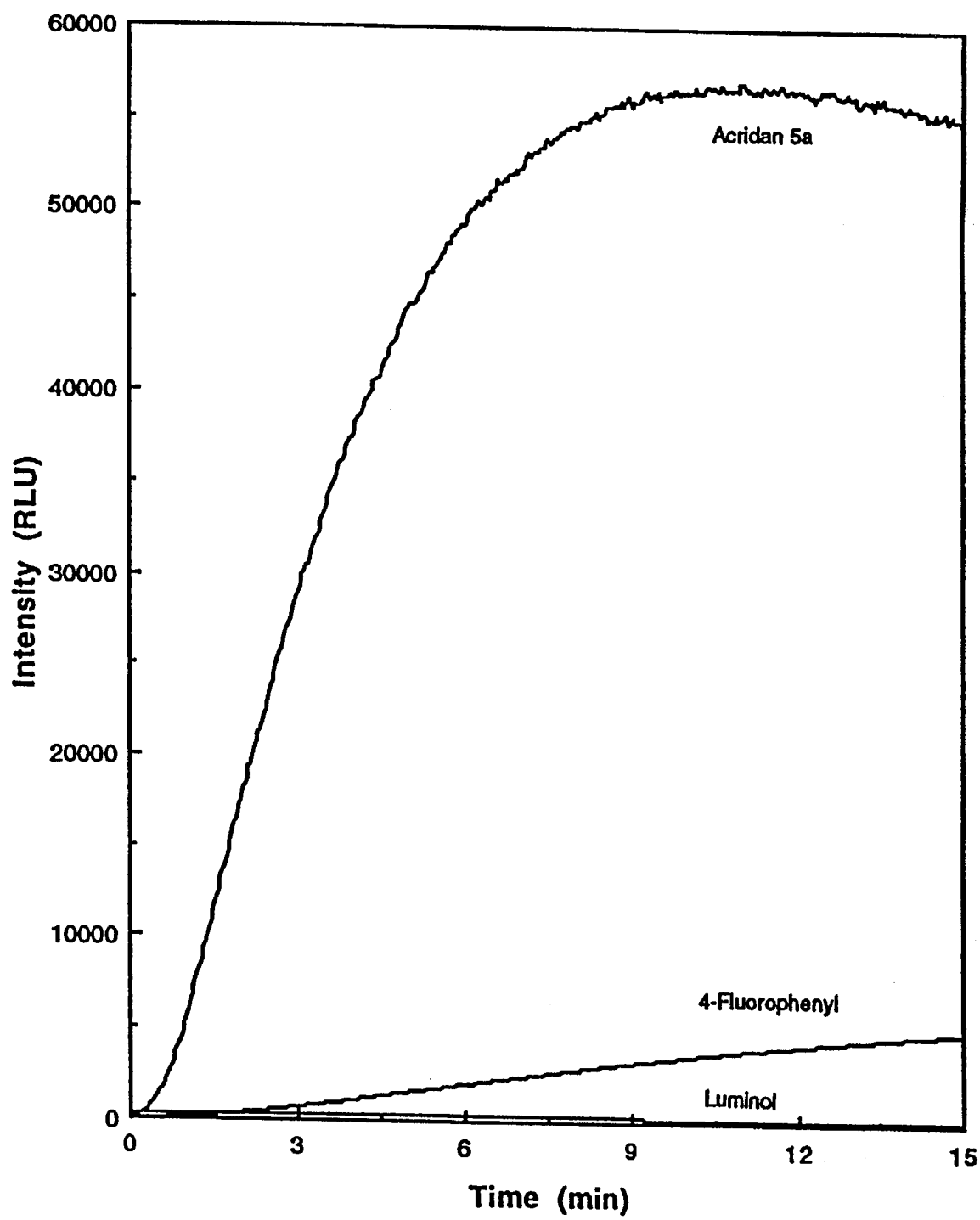
FIG. 1 is a graph showing a comparison of the light emission profiles from a reagent containing 2',6'-difluorophenyl 10-methyl-acridan-9-carboxylate (5a) of the present invention, a reagent containing the acridan 4'-fluorophenyl 10-methylacridan-9-carboxylate and a commercial reagent containing luminol. Forty µL each of three formulations were reacted in separate experiments with 1 µL of a solution containing $1.4 \times 10^{-16}$ mol of HRP in water. These formulations consisted of: (1) 0.05 mM acridan compound 5a in 0.01M tris buffer, pH 8.0, 0.4 mM urea peroxide, 0.1 mM p-phenylphenol, 0.025% TWEEN 20, 1 mM EDTA; (2) an identical formulation containing 4'-fluorophenyl 10-methylacridan-9-carboxylate in place of 5a and (3) an optimized reagent containing luminol (AMERSHAM ECL, Amersham, PLC, Amersham, U.K.).
Figure 2:
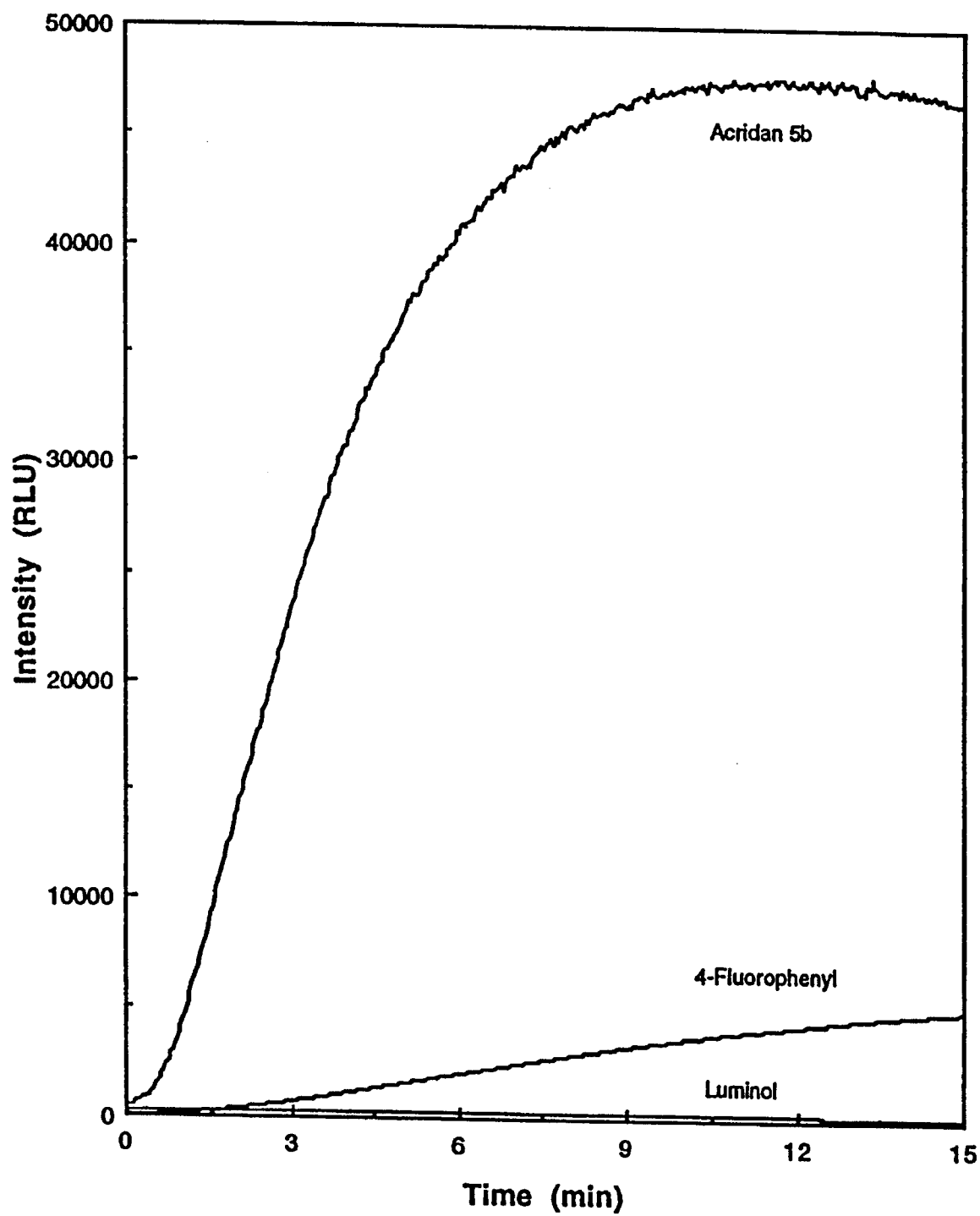
FIG. 2 is a graph showing a comparison of the light emission profiles from a reagent containing 3',5'-difluorophenyl10-methylacridan-9-carboxylate (5b) of the present invention, a reagent containing the acridan 4'-fluorophenyl 10-methylacridan-9-carboxylate and a commercial reagent containing luminol. Forty µL each of three formulations were reacted in separate experiments with 1 µL of a solution containing $1.4 \times 10^{-16}$ mol of HRP in water. These formulations consisted of: (1) 0.05 mM acridan compound 5b in 0.01M tris buffer, pH 8.0, 0.4 mM urea peroxide, 0.1 mM p-phenylphenol, 0.025% TWEEN 20, 1 mM EDTA; (2) an identical formulation containing 4'-fluorophenyl 10-methylacridan-9-carboxylate in place of 5b and (3) an optimized reagent containing luminol.
Figure 3:
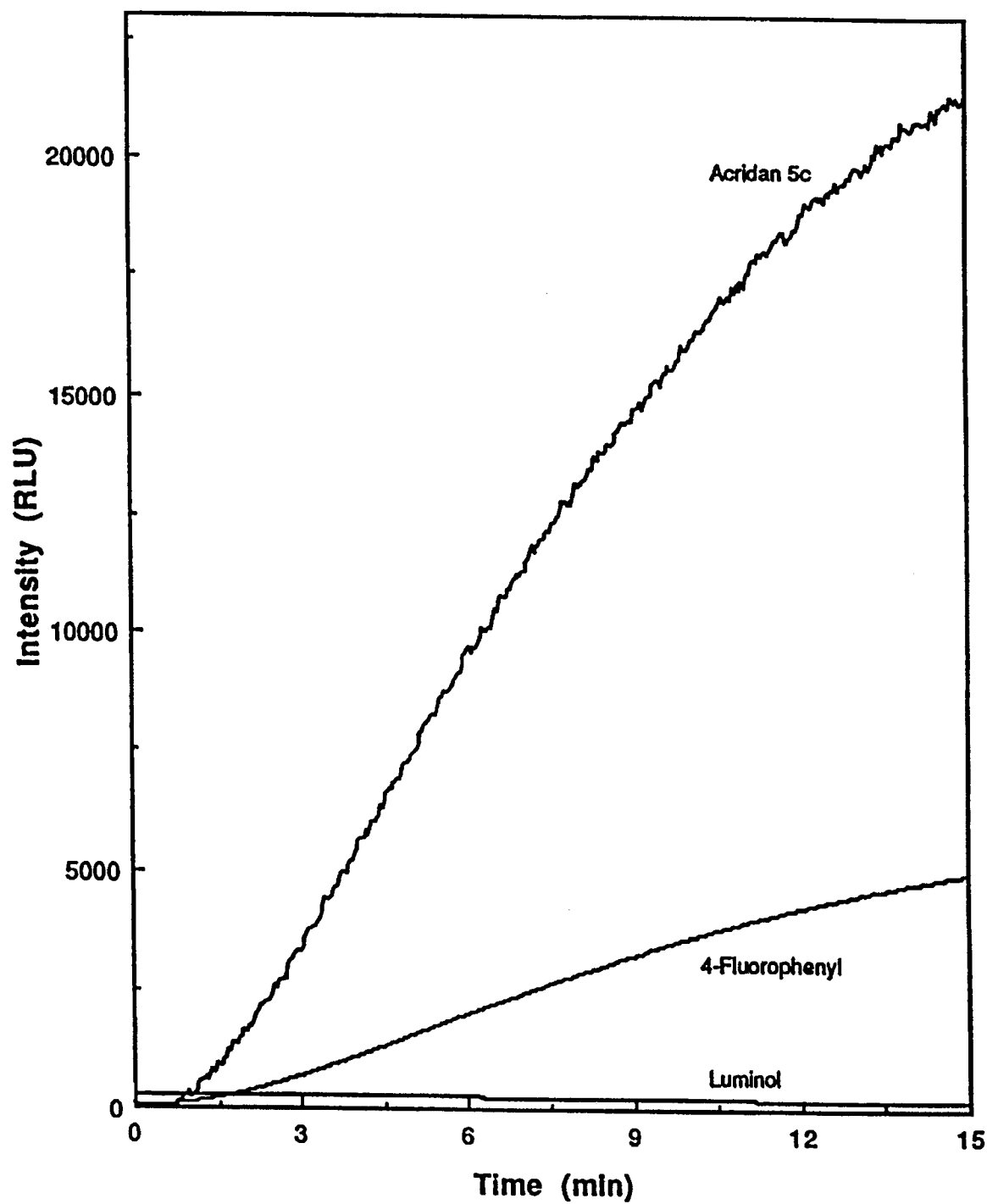
FIG. 3 is a graph showing a comparison of the light emission profiles from a reagent containing 2',4',6'-trichlorophenyl 10-methylacridan-9-carboxylate (5c) of the present invention, a reagent containing the acridan 4'-fluorophenyl 10-methylacridan-9-carboxylate and a commercial reagent containing luminol. Forty µL each of three formulations were reacted in separate experiments with 1 µL of a solution containing $1.4 \times 10^{-16}$ mol of HRP in water. These formulations consisted of: (1) 0.05 mM acridan compound 5c in 0.01M tris buffer, pH 8.0, 0.4 mM urea peroxide, 0.1 mM p-phenylphenol, 0.025% TWEEN 20, 1 mMEDTA; (2) an identical formulation containing 4'-fluorophenyl 10-methylacridan-9-carboxylate in place of 5c and (3) an optimized reagent containing luminol.
Figure 4:
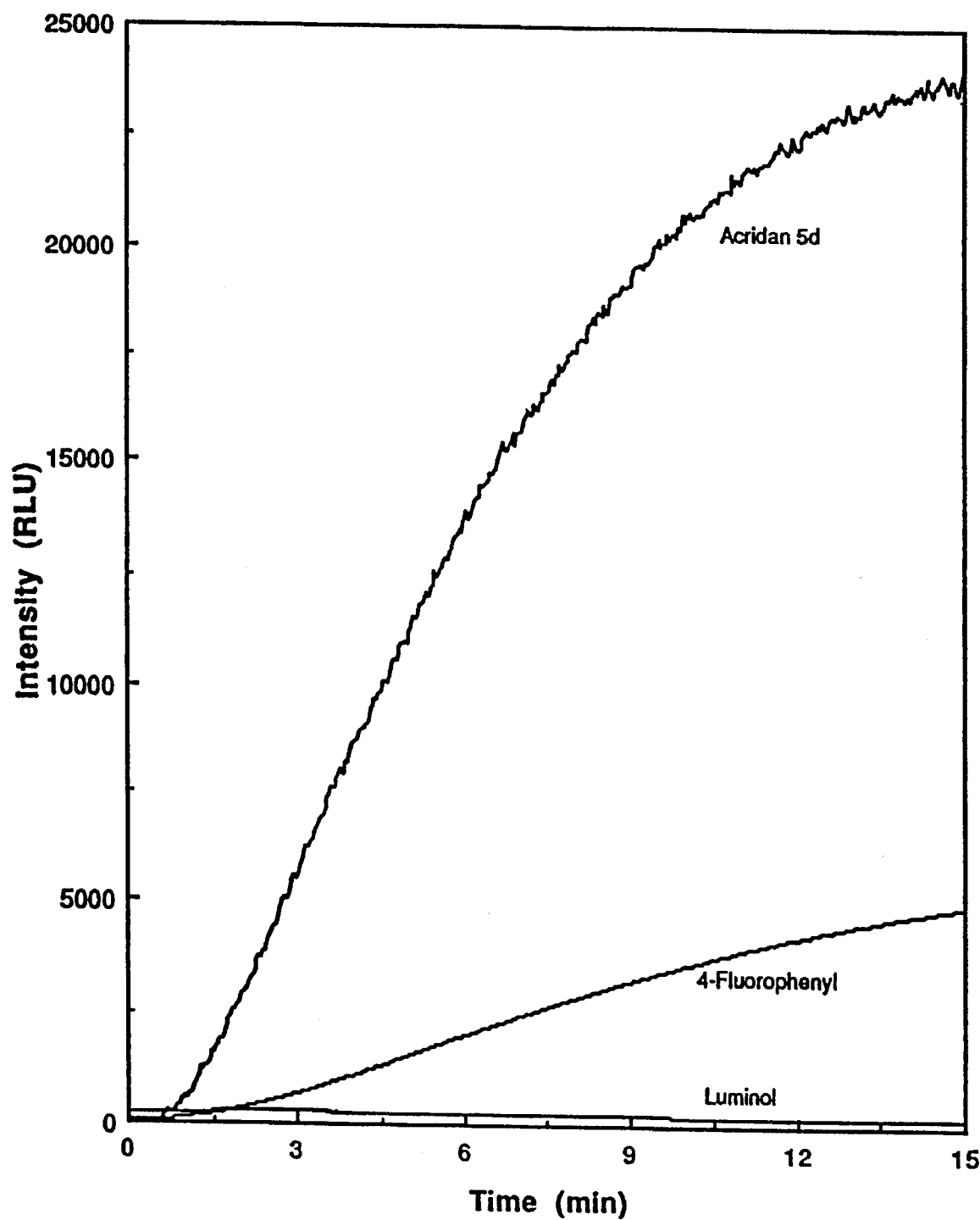
FIG. 4 is a graph showing a comparison of the light emission profiles from a reagent containing 2',4',5'-trichlorophenyl 10-methylacridan-9-carboxylate (5d) of the present invention, a reagent containing the acridan 4'-fluorophenyl 10-methylacridan-9-carboxylate and a commercial reagent containing luminol. Forty µL each of three formulations were reacted in separate experiments with 1 µL of a solution containing $1.4 \times 10^{-16}$ mol of HRP in water. These formulations consisted of: (1) 0.05 mM acridan compound 5d in 0.01M tris buffer, pH 8.0, 0.4 mM urea peroxide, 0.1 mM p-phenylphenol, 0.025% TWEEN 20, 1 mM EDTA; (2) an identical formulation containing 4'-fluorophenyl 10-methylacridan-9-carboxylate in place of 5d and (3) an optimized reagent containing luminol.
Figure 5:
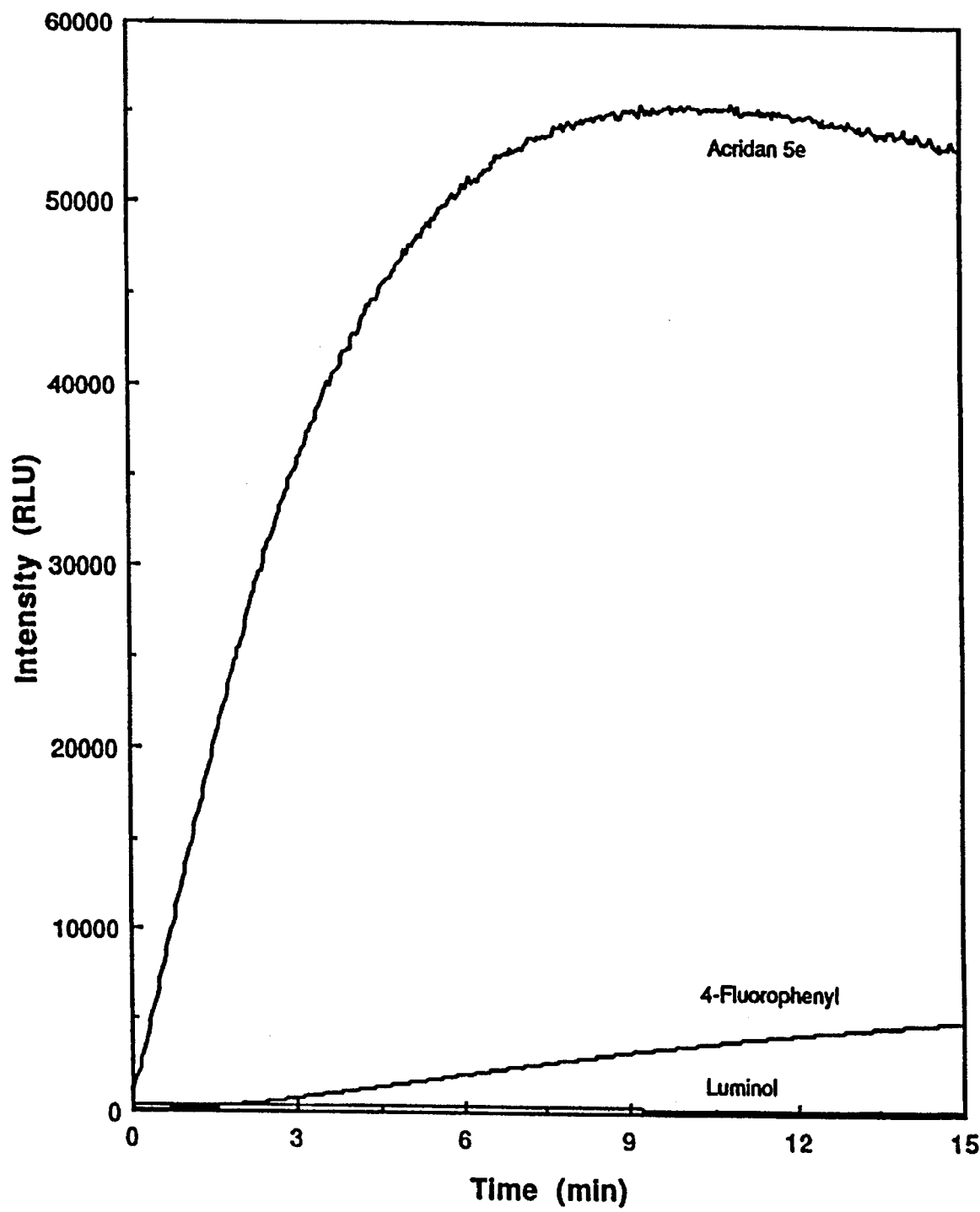
FIG. 5 is a graph showing a comparison of the light emission profiles from a reagent containing 2',3',6'-trifluorophenyl 10-methylacridan-9-carboxylate (5e) of the present invention, a reagent containing the acridan 4'-fluorophenyl 10-methylacridan-9-carboxylate and a commercial reagent containing luminol. Forty μL each of three formulations were reacted in separate experiments with 1 μL of a solution containing $1.4 \times 10^{-16}$ mol of HRP in water. These formulations consisted of: (1) 0.05 mM acridan compound 5e in 0.01M tris buffer, pH 8.0, 0.4 mM urea peroxide, 0.1 mM p-phenylphenol, 0.025% TWEEN 20, 1 mM EDTA; (2) an identical formulation containing 4'-fluorophenyl 10-methylacridan-9-carboxylate in place of 5e and (3) an optimized reagent containing luminol.
Figure 6:
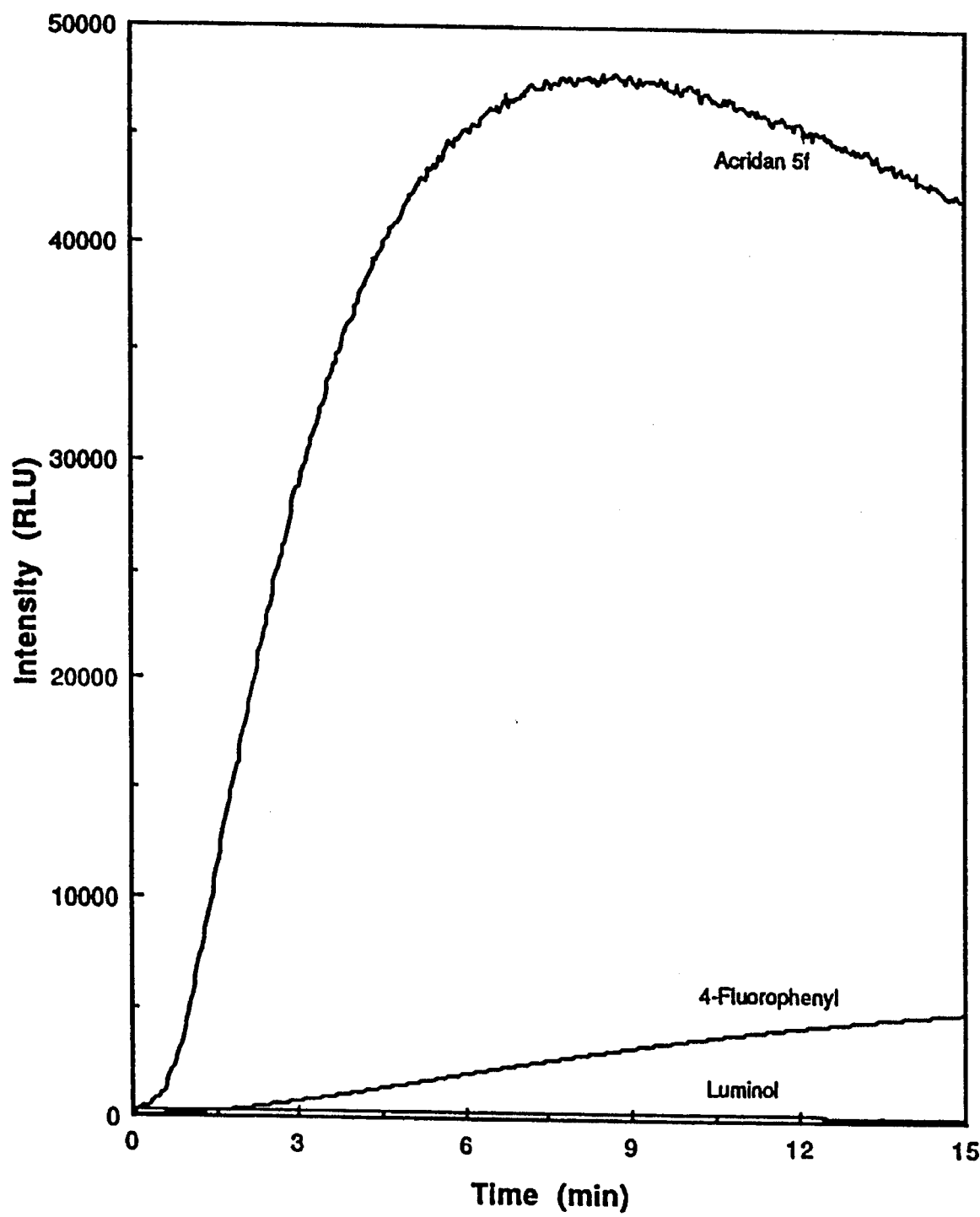
FIG. 6 is a graph showing a comparison of the light emission profiles from a reagent containing pentafluorophenyl 10-methylacridan-9-carboxylate (5f) of the present invention, a reagent containing the acridan 4'-fluorophenyl 10-methylacridan-9-carboxylate and a commercial reagent containing luminol. Forty μL each of three formulations were reacted in separate experiments with 1 μL of a solution containing $1.4 \times 10^{-16}$ mol of HRP in water. These formulations consisted of: (1) 0.05 mM acridan compound 5f in 0.01M tris buffer, pH 8.0, 0.4 mM urea peroxide, 0.1 mM p-phenylphenol, 0.025% Tween 20, 1 mM EDTA; (2) an identical formulation containing 4'-fluorophenyl 10-methylacridan-9-carboxylate in place of 5f and (3) an optimized reagent containing luminol.
Figure 7:
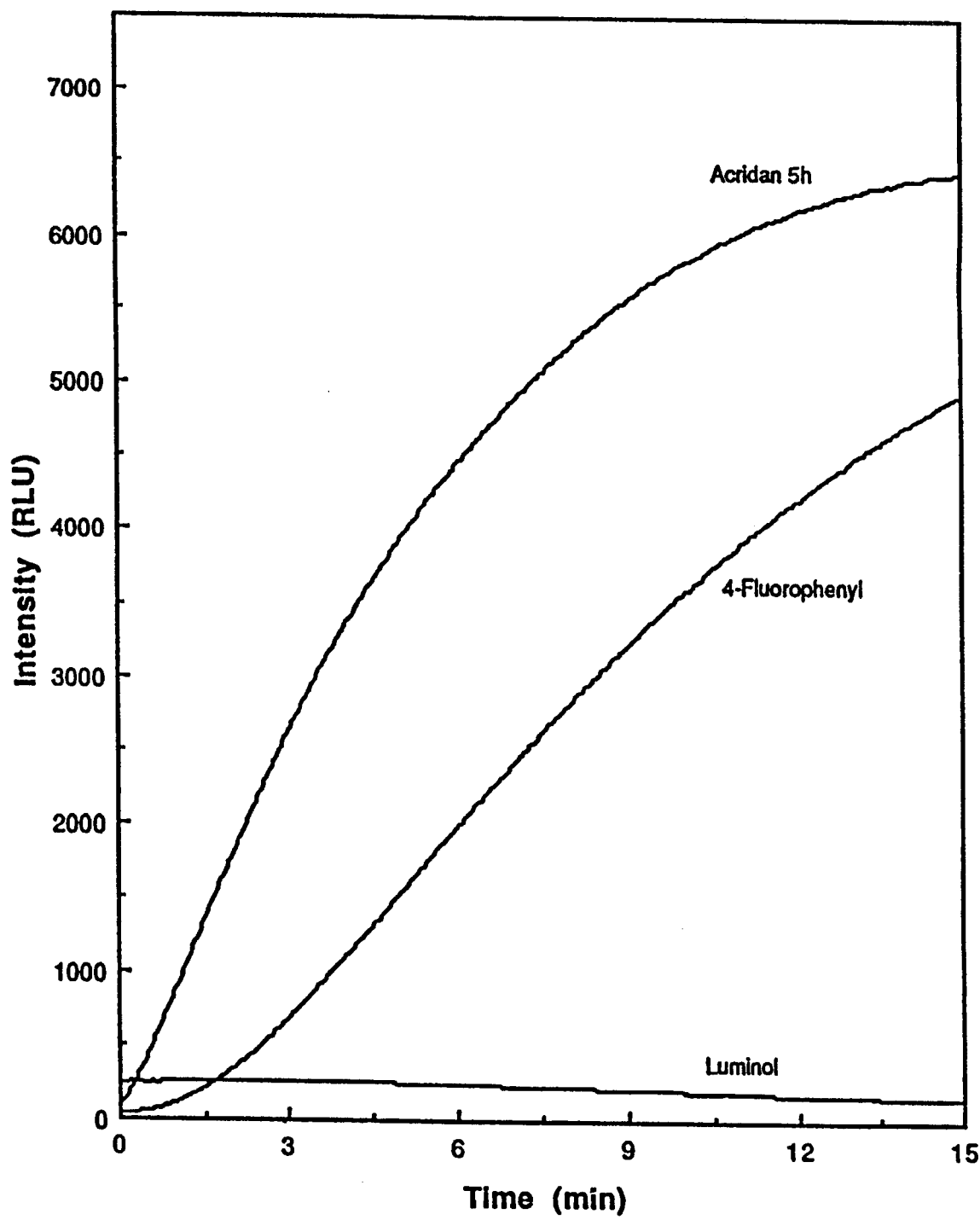
FIG. 7 is a graph showing a comparison of the light emission profiles from a reagent containing 2',3',6'-trifluorophenyl 3-methoxy-10-methylacridan-9-carboxylate (5h) of the present invention, a reagent containing the acridan 4'-fluorophenyl 10-methylacridan-9-carboxylate and a commercial reagent containing luminol. Forty μL each of three formulations were reacted in separate experiments with 1 μL of a solution containing $1.4 \times 10^{-16}$ mol of HRP in water. These formulations consisted of: (1) 0.05 mM acridan compound 5h in 0.01M tris buffer, pH 8.0, 0.4 mM urea peroxide, 0.1 mM p-phenylphenol, 0.025% TWEEN 20, 1 mM EDTA; (2) an identical formulation containing 4'-fluorophenyl 10-methylacridan-9-carboxylate in place of 5h and (3) an optimized reagent containing luminol.

The chemiluminescent detection of peroxidase and peroxide with acridans of the formula:

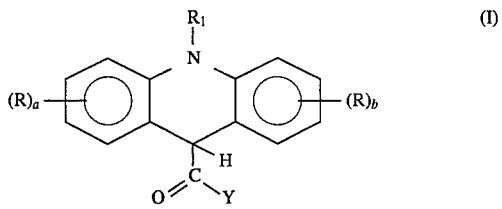
(I)

wherein $R_1$ is selected from alkyl, heteroalkyl and aralkyl groups, wherein R is any group which allows the production of light and a and b are integers between 0 and 4 and wherein Y is a leaving group which allows the production of light (chemiluminescence) from the acridan by reaction with a peroxide and a peroxidase were disclosed in applicants' co-pending application Ser. No. 08/061,810 filed on May 17, 1993. It has now been discovered that certain acridan derivatives including di- and polyhaloaryl ester derivatives (Formula I, Y=OArX$_n$) provide superior properties in producing chemiluminescence.

The present invention relates particularly to an improved acridan of the formula:

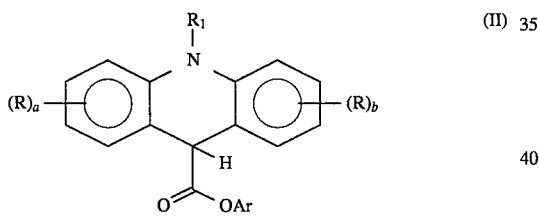
(II)

wherein $R_1$ is selected from alkyl, heteroalkyl and aralkyl groups, wherein R is any group which allows the production of light and a and b are integers between 0 and 4 and wherein Ar—O is a leaving group wherein Ar—O is selected from the group consisting of di- and polyhalosubstituted phenoxy groups which allows the production of light from the acridan by reaction with a peroxide and a peroxidase. Ar—O groups containing at least two halogen substituents provide unexpectedly superior performance in producing chemiluminescence and in assays.

The present invention relates to an improvement in a reagent composition which generates light in the presence of a peroxidase which comprises:

a) an acridan of the formula:

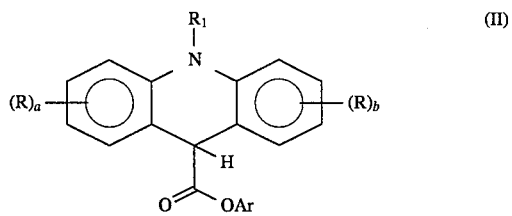
(II)

wherein $R_1$ is selected from the group consisting of alkyl, heteroalkyl and aralkyl groups, wherein R is any group which allows the production of light and a and b are integers between 0 and 4 and wherein Ar—O is a leaving group wherein Ar—O is selected from the group consisting of di- and polyhalosubstituted phenoxy groups which allows the production of light from the acridan by reaction with a peroxide and a peroxidase;

b) optionally a phenolic compound which enhances light production from the acridan;

c) a peroxide compound which participates in the reaction of the acridan with the peroxidase;

d) a chelating agent which prevents the peroxide compound from reacting prior to addition of the peroxidase to the composition; and e) a surfactant.

The present invention relates to an improved method for producing, chemiluminescence which comprises reacting a peroxide compound and a peroxidase enzyme with an acridan of the formula:

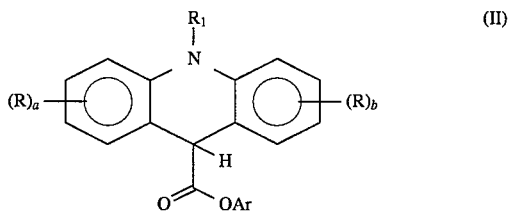
(II)

wherein $R_1$ is selected from the group consisting of alkyl, heteroalkyl and aralkyl groups, wherein R is any group which allows the production of light and a and b are integers between 0 and 4 and wherein Ar—O is a leaving group wherein Ar—O is selected from the group consisting of di- and polyhalosubstituted phenoxy groups which allows the production of light from the acridan by reaction with a peroxide and a peroxidase.

The present invention also relates to an improved method for detecting a peroxidase enzyme or an analyte linked to or capable of being linked to a peroxidase enzyme in an assay procedure by a chemiluminescent reaction, the improvement which comprises reacting an acridan with a peroxide and a peroxidase enzyme to produce light for detecting the analyte wherein the acridan is of the following formula:

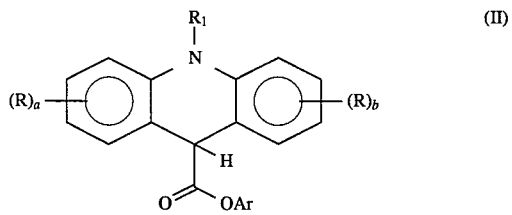
(II)

wherein $R_1$ is selected from the group consisting of alkyl, heteroalkyl and aralkyl groups, wherein R is any group which allows the production of light and a and b are integers between 0 and 4 and wherein Ar—O is a leaving group wherein Ar—O is selected from the group consisting of di- and polyhalosubstituted phenoxy groups which allows the production of light from the acridan by reaction with a peroxide and a peroxidase.

The present invention also relates to an improved method for detecting a peroxidase enzyme or an analyte linked to or capable of being linked to a peroxidase enzyme in an assay procedure by a chemiluminescent reaction, the improvement which comprises:

a) providing a reagent composition which generates light in the presence of a peroxidase which comprises: an acridan of the formula:

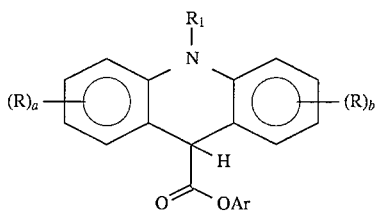

wherein $R_1$ is selected from the group consisting of alkyl, heteroalkyl and aralkyl groups, wherein R is any group which allows the production of light and a and b are integers between 0 and 4 and wherein Ar—O is a leaving group wherein Ar—O is selected from the group consisting of di- and polyhalosubstituted phenoxy groups which allows the production of light from the acridan by reaction with a peroxide and a peroxidase; a peroxide compound which participates in the reaction of the acridan with the peroxidase; an enhancer substance which may be a phenolic compound which enhances the light production from the acridan; a chelating agent which prevents the peroxide compound from reacting prior to addition of the peroxidase to the composition; and a surfactant; and b) adding a peroxidase to the reagent composition so that light is produced for detecting the analyte.

The present invention also relates to a kit for detecting an analyte in an assay procedure by a chemiluminescent reaction to produce light which comprises in separate containers:

a) an acridan of the formula:

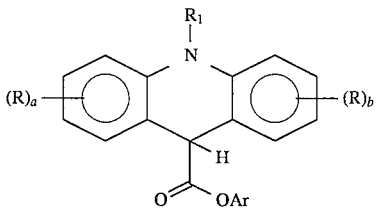

wherein $R_1$ is selected from the group consisting of alkyl, heteroalkyl and aralkyl groups, wherein R is any group which allows the production of light and a and b are integers between 0 and 4 and wherein Ar—O is a leaving group wherein Ar—O is selected from the group consisting of di- and polyhalosubstituted phenoxy groups which allows the production of light from the acridan by reaction with a peroxide and a peroxidase; a peroxide; optionally an enhancer substance which may be a phenolic compound which enhances the light production from the acridan; optionally a chelating agent which prevents the peroxide compound from reacting prior to addition of the peroxidase to the composition; and a surfactant; and b) a peroxidase enzyme, wherein the light is detected in the assay procedure by reacting the reagent composition with the peroxidase.

The present invention also relates to an improved method for detecting hydrogen peroxide in an assay procedure by a chemiluminescent reaction, the improvement which comprises reacting hydrogen peroxide and a peroxidase enzyme with an acridan of the formula:

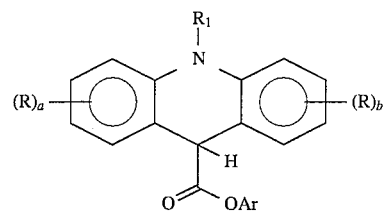

wherein $R_1$ is selected from the group consisting of alkyl, heteroalkyl and aralkyl groups, wherein R is any group which allows the production of light and a and b are integers between 0 and 4 and wherein Ar—O is a leaving group wherein Ar—O is selected from the group consisting of di- and polyhalosubstituted phenoxy groups which allows the production of light from the acridan by reaction with a peroxide and a peroxidase.

The invention involves improved N-alkylacridancarboxylate derivatives with superior properties in one or more of the following characteristics: longer duration of light emission, higher intensity of light emission, faster rate of rise of light emission to the maximum value, lowered background chemiluminescence, improved signal/background ratio, extended storage stability of a chemiluminescent detection reagent composition, enhanced light emission on a membrane or other properties. The particular combinations of the groups R and Ar are chosen so as to provide a compound with one or more properties which are optimal for particular applications. In particular, N-alkylacridancarboxylate derivatives with Ar groups bearing two or more halogen substituents are unexpectedly superior in light generating properties. It is thought that the incorporation of two or more halogen substituents in the Ar moiety produces an acridan with a better leaving group thereby accelerating and promoting the chemiluminescent reaction at the expense of competing non-chemiluminescent side reactions.

In general when more rapid build-up of light intensity or higher peak light intensity are desired it is advantageous to select the O—Ar group such that the $pK_a$ of the conjugate acid (Ar—OH) of the Ar—O— anion is lower than that of Ph—OH, preferably less than about 9.5. Examples include phenols or phenolic compounds (Ar—OH) which are substituted with $pK_a$-lowering electron withdrawing groups such as halogen atoms and hence are more ionized at a given pH. As a result they tend to function as better leaving groups in nucleophilic displacement reactions such as the replacement of the OAr group of an ester by a nucleophile such as water, hydroxide ion or peroxy anion. When extended storage stability of a chemiluminescent reagent composition containing an N-alkylacridancarboxylate derivative is desired, one or more of the groups R may be a group such as an alkyl, alkoxy or aryloxy group.

Examples of some preferred compounds are:

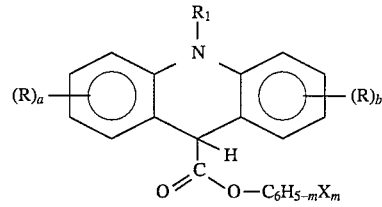

wherein X is a halogen atom selected from F, Cl, Br or I and m is 2 to 5.

Another class of preferred compounds are:

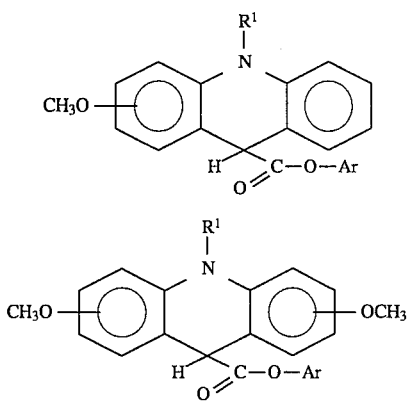

more preferred are:

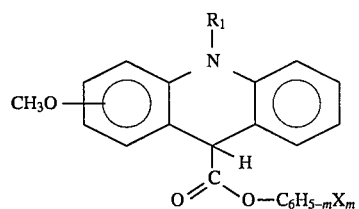

wherein X is a halogen atom selected from F, Cl, Br or I and m is 2 to 5.

Additional acridan compounds which have been prepared and tested for light production include phenyl 10-methylacridan-9-carboxylate; 2',6'-dimethylphenyl 10-methylacridan-9-carboxylate; 4'-fluorophenyl 10-methylacridan-9-carboxylate; 4'-iodophenyl 10-methylacridan-9-carboxylate; 4'-phenylphenyl 10-methylacridan-9-carboxylate; 3',5'-dicarbomethoxyphenyl10-methylacridan-9-carboxylate; 4'-(N-butylaminocarbonyl)phenyl 10-methylacridan-9-carboxylate; 4'-methoxyphenyl 10-methylacridan-9-carboxylate; 2',6'-dimethoxyphenyl 10-methylacridan-9-carboxylate; 4'-acetamidophenyl 10-methylacridan-9-carboxylate; 4'-(2-(succinimidyloxycarbonyl)ethyl)phenyl 10-methylacridan-9-carboxylate; 2'-hydroxyphenyl 10-methylacridan-9-carboxylate; 3'-hydroxyphenyl10-methylacridan-9-carboxylate; 4'-hydroxyphenyl 10-methylacridan-9-carboxylate; 2',6'-dihydroxyphenyl 10-methylacridan-9-carboxylate; 2',3'-dihydroxyphenyl 10-methylacridan-9-carboxylate; 2',3',5',6'-tetrafluoro-4'-hydroxyphenyl 10-methylacridan-9-carboxylate; naphthyl 10-methylacridan-9-carboxylate and 6'-hydroxynaphthyl 10-methylacridan-9-carboxylate. These compounds were less effective than those of the present invention.

Reaction of certain N-alkylacridancarboxylate derivatives of the present invention with a peroxide and a peroxidase enzyme produces chemiluminescence with superior properties for assay applications. The chemiluminescence is believed to arise from the excited state of N-alklyacridone or the substituted N-alklyacridone product as shown in the generalized reaction below.

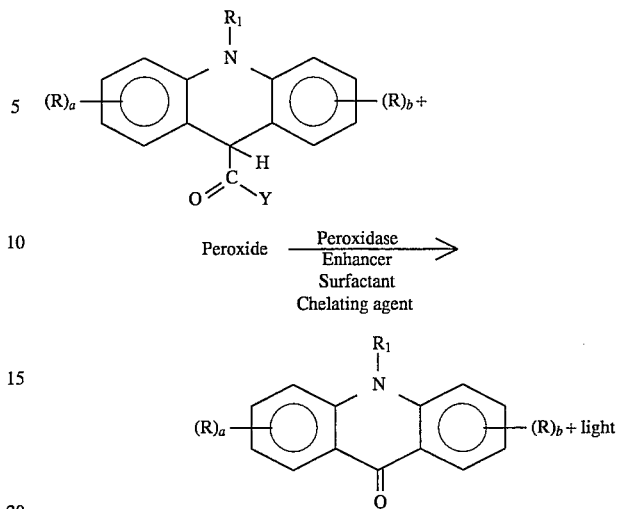

The present invention involves a method of generating chemiluminescence from the oxidation of N-alkylacridancarboxylic acid derivatives by the action of a peroxidase enzyme, a peroxide compound and enhancers. The invention also relates to the use of this method to detect the peroxidase enzyme with high sensitivity. Further, the invention relates to the use of the method to detect and quantitate various biological molecules which are bound to this enzyme by chemical bonds or through physical interactions. Further, the invention relates to the use of the method to detect and quantitate various biological molecules which are capable of being bound to this enzyme, for example, by using a biotin-labeled analyte and streptavidin-peroxidase conjugate. Other high affinity binding pairs well known in the art such as fluorescein and anti-fluorescein, digoxigenin and anti-digoxigenin or complementary nucleic acid sequences may also be readily employed as a means of linking a peroxidase enzyme to an analyte for the purpose of practicing this invention. The intensity of the resulting chemiluminescence provides a direct measure of the quantity of labeled organic or biological molecule. For example, the method may be used to detect haptens, antigens and antibodies by the technique of immunoassay, proteins by Western blotting, DNA and RNA by Southern and Northern blotting, respectively. The method may also be used to detect DNA in DNA sequencing applications. The method may additionally be used to detect hydrogen peroxide generated by enzymes such as cholesterol oxidase, glucose oxidase, glucose-6-phosphate dehydrogenase, galactose oxidase, galactose-6-phosphate dehydrogenase, and amino acid oxidase. The method may also therefore be used as a means to detect the enzymes mentioned above which generate hydrogen peroxide.

The reaction of the present invention may advantageously be carried out in solution such as an aqueous buffer or on the surface of a solid support such as a bead, tube, microwell plate or a membrane. Suitable buffers include any of the commonly used buffers capable of maintaining a pH in the range of about 7 to about 10 for example, phosphate, borate, carbonate, tris(hydroxymethylamino)methane, glycine, tricine, 2-amino-2-methyl-1-propanol, diethanolamine and the like. The preferred method of practicing the invention in this regard is determined by the requirements of the particular intended use as in for example, immunoassays, Western blotting, Southern blotting etc. When the detection is to be performed on a membrane, said membrane may optionally be provided in a kit.

The detection of chemiluminescence from the oxidation of an N-alkylacridancarboxylate derivative by hydrogen peroxide and a peroxidase enzyme can be accomplished with good sensitivity. Enhancement of this reaction by incorporation of chemiluminescence-enhancing substances permits the measurement of chemiluminescence using still lower levels of the peroxidase enzyme. Coupling this enzyme to a biological molecule of interest then permits the detection of this biological molecule with great sensitivity.

Incorporation of certain substituted phenolic compounds either alone or in combination with surfactants into the reaction mixture enhances the chemiluminescence produced in the presence of added peroxidase and peroxide. Enhancement may take the form of either a higher light intensity, or light emission of longer duration or both. Phenolic compounds which are known to enhance other peroxidase reactions and which are found to enhance the amount of chemiluminescence in the present invention include but are not limited to: p-phenylphenol, p-iodophenol, p-bromophenol, p-hydroxycinnamic acid, 2-naphthol and 6-bromo-2-naphthol. It will be obvious to one knowledgeable in the art that other phenolic and aromatic amine compounds fall within the scope of this invention. Such compounds include firefly luciferin, 6-hydroxybenzothiazole, 2-cyano-6-hydroxybenzothiazole, 4-(4-hydroxyphenyl)thiazole, p-chlorophenol, 2,4-dichlorophenol, 2-chloro-4-phenylphenol, 1-bromo-2-naphthol 1,6-dibromo-2-naphthol, 2-hydroxy-9-fluorenone, 6-hydroxybenzoxazole derivatives, and 4-hydroxy-3-[3-(4-hydroxyphenyl) 1-oxo-2-propenyl]-2H-1-benzopyran-2-one as are described in, for example, G. Thorpe, L. Kricka, in Bioluminescence and Chemiluminescence, New Perspectives, J. Scholmerich, et al, Eds., pp. 199–208 (1987), M. Ii, H. Yoshida, Y. Aramaki, H. Masuya, T. Hada, M. Terada, M. Hatanaka, Y. Ichimori, Biochem. Biophys. Res. Comm., 193(2), 540–5 (1993), and in U.S. Pat. Nos. 5,171,668 and 5,206,149 which are incorporated herein by reference.

Additives which suppress the generation of chemiluminescence from the reaction of hydrogen peroxide and N-alkylacridancarboxylate derivatives in the absence of peroxidase enzymes are employed to further improve the utility of the invention. It has also been found that certain compounds including cyclodextrins and surfactants including $C_{12}$–$C_{20}$ alkyl sulfates and sulfonates, dextran sulfate, $C_{12}$–$C_{20}$ alkyltrimethylammonium salts, and nonionic surfactants including polyoxyalkylene alkylphenols, polyoxyalkylene alcohols, polyoxyealkylene ethers, polyoxyalkylene sorbitol esters and the like improve the sensitivity of detection of the peroxidase enzyme in assays of the present invention by providing a better signal to background ratio. The improvement occurs through minimizing the background chemiluminescence in the absence of added peroxidase, possibly due to a slowing of the autoxidative decomposition of the acridan derivative.

The preferred amounts of the various components of a composition of the present invention are set forth in Table I.

TABLE I

| Acridan 5 | 0.01–10 mM |
|---|---|
| Phenol enhancer | 0.001–10 mM |
| Surfactant | 0.005–5% |
| Peroxide | 0.01–10 mM |
| Chelating agent | 0.01–5 mM |

The present invention involves a solution in an aqueous buffer containing 1) a phenol enhancer or a salt of a phenol enhancer, 2) a peroxide compound wherein the peroxide compound may be hydrogen peroxide, urea peroxide, or a perborate salt, 3) an acridan compound of the invention, 4) a cation complexing agent wherein the agent may be selected from the group consisting of chelating agents such as ethylenediaminetetraacetic acid (EDTA), diethylenetriaminepentaacetic acid (DTPA), or ethylenebis(oxyethylenenitrilo)-tetraacetic acid (EGTA) and their salts, and 5) a surfactant such as the anionic surfactant sodium dodecyl sulfate (SDS), or preferably a nonionic surfactant such as polyoxyethylenated alkylphenols, polyoxyethylenated alcohols, polyoxyethylenated ethers, polyoxyethylenated sorbitol esters and the like.

In a preferred method of practicing the present invention, an aqueous buffer solution with a pH in the range of 7–10 containing a phenol compound such as p-phenylphenol at a final concentration from about 0.01M to $1\times10^{-6}$M, a nonionic surfactant at a final concentration from about 5% to 0.005% (v/v), a peroxide source such as hydrogen peroxide or, preferably, a perborate salt or urea peroxide and a cation complexing agent such as EDTA at a final concentration from about $1\times10^{-3}$M to $1\times10^{-5}$M is mixed with a second solution containing an acridan compound of the invention to achieve a final concentration from about 0.001M to $1\times10^{-5}$M to form the detection reagent solution. This solution is contacted with the peroxidase enzyme which may either be in solution or adhered to a solid support. Optimum concentrations of reagents must be determined individually for each composition. The concentration of acridan compound and enhancer in particular should be optimized with care for each case in order to produce the maximum enhancement of light emission. The detection reaction may be performed over a range of temperatures including at least the range 20°–40° C. Detection may be conveniently and advantageously carried out at ambient temperature.

It has further been discovered that the storage life of the detection reagent composition can be significantly extended by excluding oxygen from the solution. Detection reagents of the present invention stored in this manner retain the ability to generate the same quantity of chemiluminescence by the action of a peroxidase enzyme for longer periods of time. Extended storage stability can result in savings in reagents and cost.

Significant advantages of N-alkylacridancarboxylate derivatives and compositions of the present invention containing them are increased sensitivity of detection of the peroxidase enzyme and increased stability of the N-alkylacridancarboxylate derivative to hydrolytic decomposition. Comparative experiments show a 100-fold lowering of the detection limit of HRP using a reagent composition of this invention compared to a detection reagent containing luminol and an enhancer. An additional advantage is the wider dynamic range of measurement of peroxidase concentration. An additional advantage of N-alkylacridancarboxylate derivatives is their thermal and photochemical stability and ease of purification. The most widely known chemiluminescent substrates for peroxidase enzymes known in the prior art, aminoaryl cyclic diacylhydrazides such as luminol are difficult to prepare and maintain in a state of high purity and must either be protected from light or purified immediately before use (R. A. W. Stott, L. J. Kricka, Bioluminescence and Chemiluminescence, New Perspectives, J. Scholmerich, et al, Eds., pp. 237–240 (1987)). Still another advantage of the use of certain N-alkylacridancarboxylate derivatives compared to prior compounds is the extended duration of chemiluminescence. Extending the duration simplifies the measurement by obviating the need for precise reaction timing and increases the sensitivity of detection when using film-based detection methods.

EXAMPLES

Example 1

Synthesis of Acridan Derivatives

Acridancarboxylate derivatives 5a–j were synthesized according to the method shown in Scheme 1 from the corresponding acridine-9-carboxylic acid. In the structure shown below the groups $(R)_a$ in formula (II) are all hydrogen except as otherwise specified by the substituent A, the groups $(R)_b$ in formula (II) are all hydrogen except as otherwise specified by the substituent B.

| Compound | A | B | Ar |
|---|---|---|---|
| 5a | H | H | 2,6-difluorophenyl |
| 5b | H | H | 3,5-difluorophenyl |
| 5c | H | H | 2,4,6-trichlorophenyl |
| 5d | H | H | 2,4,5-trichlorophenyl |
| 5e | H | H | 2,3,6-trifluorophenyl |
| 5f | H | H | pentafluorophenyl |
| 5g | 2-OCH₃ | H | 2,3,6-trifluorophenyl |
| 5h | 3-OCH₃ | H | 2,3,6-trifluorophenyl |
| 5i | 3-OCH₃ | H | 2,6-difluorophenyl |
| 5j | 2-OCH₃ | 7-OCH₃ | 2,3,6-trifluorophenyl |

The corresponding acridine-9-carboxylic acid compounds 1, when not commercially available, were prepared by the reaction sequence depicted in Scheme 2. (G. Zomer, J. Stavenuiter, R. Van Den Berg, E. Jansen, In Luminescence Techniques in Chemical and Biochemical Analysis, W. Baeyens, D. De Keukeleire, K. Korkidis, eds., Dekker, N.Y., 505–521, (1991); R. Stoll, J. Prakt. Chem., 105, 137, (1922)).

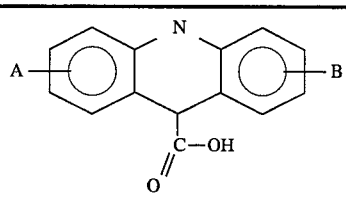

| Compound | A | B |
|---|---|---|
| 1a | H | H |
| 1f | 2-OCH₃ | H |
| 1g | 3-OCH₃ | H |
| 1i | 2-OCH₃ | 7-OCH₃ |

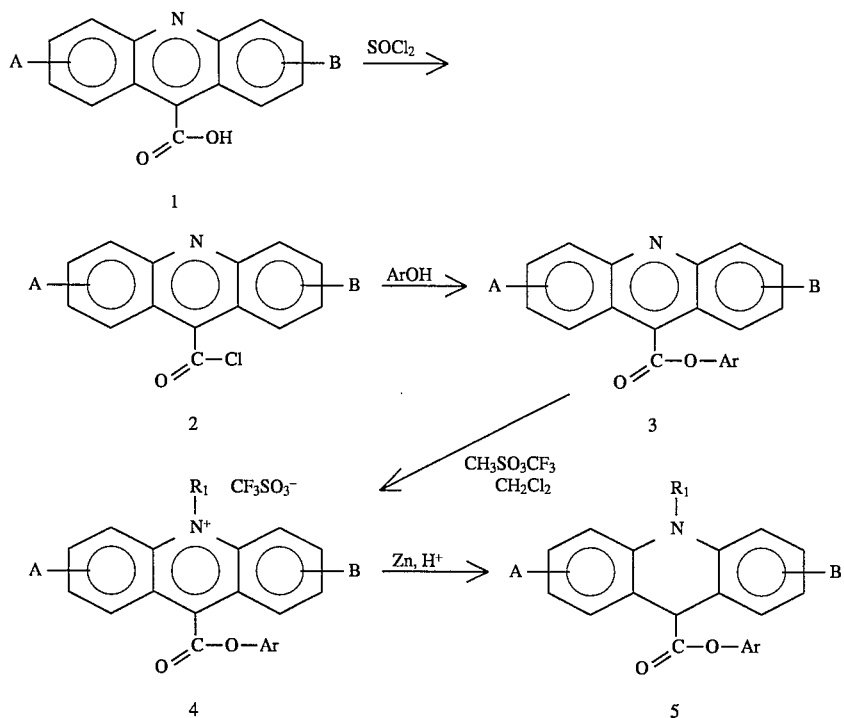

Scheme 1.

Scheme 2.

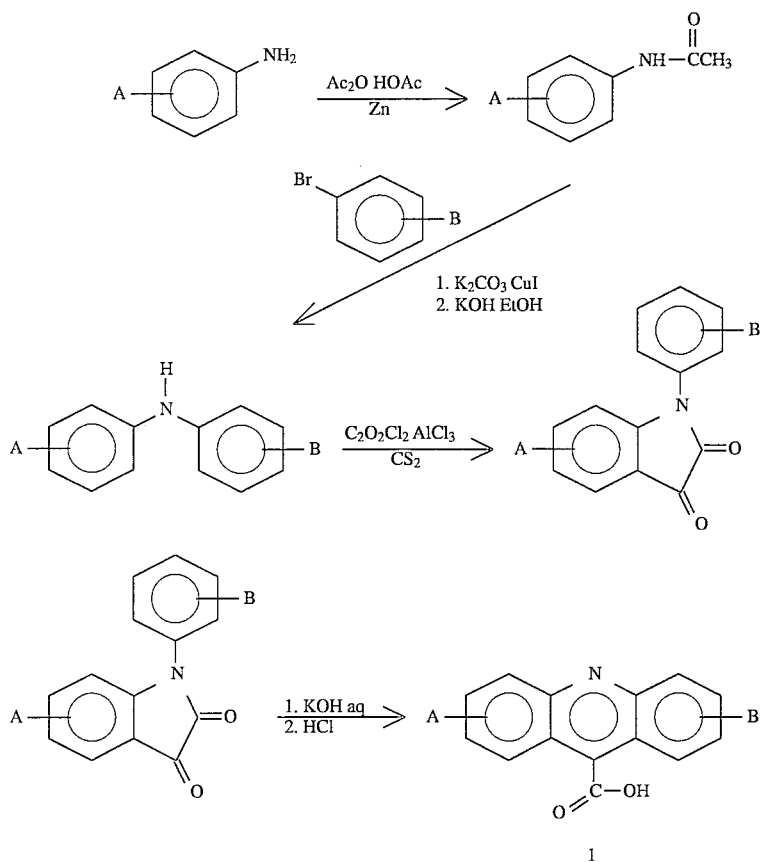

General Procedure for Synthesis of Compound 3. Acridine-9-carboxylic acid (Compound 1a, Aldrich, 0.2–0.5 g) was suspended in excess thionyl chloride (3–10 mL) and reaction mixture was refluxed for 3 h. The solvent was removed under reduced pressure to obtain a yellow solid which was dissolved in methylene chloride and pyridine (2–3 sq.) under argon. A solution of the phenol (1–1.5 sq.) in methylene chloride was added dropwise. The solution was stirred overnight at room temperature then diluted with more methylene chloride (100 mL) and washed with water (3×50 mL). The organic layer was dried over $Na_2SO_4$ and concentrated to obtain the product.

| Compound 3 | Compound 1 | SOCl$_2$ | Phenol | | Pyridine |
|---|---|---|---|---|---|
| a | a | 0.50 g | 10 mL | 2,6-Difluoro- | 0.32 g | 0.44 g |
| b | a | 0.25 g | 10 mL | 3,5-Difluoro- | 0.16 g | 0.22 g |
| c | a | 0.50 g | 7 mL | 2,4,6-Trichloro- | 0.50 g | 0.52 g |
| d | a | 0.50 g | 7 mL | 2,4,5-Trichloro- | 0.50 g | 0.52 g |
| e | a | 0.50 g | 5 mL | 2,3,6-Trifluoro- | 0.365 g | 0.53 g |
| f | a | 0.50 g | 10 mL | Pentafluoro- | 0.454 g | 0.44 g |
| g | g | 1.20 g | 10 mL | 2,3,6-Trifluoro- | 0.80 g | 3 mL |
| h | h | 1.50 g | 10 mL | 2,3,6-Trifluoro- | 0.878 g | 0.7 mL |
| i | h | 1.70 g | 20 mL | 2,6-Difluoro- | 1.0 g | 2 mL |
| j | j | 1.0 g | 10 mL | 2,3,6-Trifluoro- | 1.4 g | 1 mL |

General Procedure for Synthesis of Compound 4. Compound 3 (1–2 mmol) was dissolved in methylene chloride (5–10 ml) under argon and methyl trifluoromethanesulfonate (5–10 sq.) was added. The solution was stirred overnight at room temperature to yield a thick yellow precipitate. This precipitate was filtered, washed with ether and dried to obtain the product as yellow crystals.

| Compound 4 | Compound 3 | | CH$_2$Cl$_2$ | CH$_3$OSO$_2$CF$_3$ | |
|---|---|---|---|---|---|
| a | a | 0.40 g | 5 mL | 0.945 mL | 7 eq. |
| b | b | 0.20 g | 5 mL | 0.472 mL | 7 eq. |
| c | c | 0.54 g | 10 mL | 1.5 mL | 10 eq. |
| d | d | 0.25 g | 10 mL | 0.70 mL | 10 eq. |
| e | e | 0.30 g | 25 mL | 0.95 mL | 10 eq. |
| f | f | 0.50 g | 15 mL | 1.0 mL | 7 eq. |
| g | g | 0.020 g | 2 mL | 0.10 mL | 19 eq. |
| h | h | 0.24 g | 3 mL | 0.10 mL | 1.4 eq. |
| i | i | 0.38 g | 5 mL | 1.0 mL | 8.8 eq. |
| j | j | 0.45 g | 10 mL | 1.0 mL | 8.8 eq. |

General Procedure for Synthesis of Compound 5 (Method A). Compound 4 (0.2–0.3 mmol) was suspended in absolute ethanol (15–30 mL) and solution was refluxed for 10 min to obtain a clear solution. Excess ammonium chloride (10–50 eq) was added by portions to the solution followed by zinc (equimolar ratio to the amount of NH$_4$Cl) causing immediate decolorization of the solution. The colorless solution was refluxed for 30 min. The cooled solution was filtered and the precipitate washed with ethanol (3×20 mL). The solution was concentrated to obtain a creamy solid which was redissolved in methylene chloride and washed with water (3×50 mL). Crude material obtained after evaporation of methylene chloride was chromatographed on silica gel (ethyl acetate/hexane) to yield the pure product as a white solid.

General Procedure for Synthesis of Compound 5 (Method B). Compound 4 (0.3–0.6 mmol) was dissolved in 10 mL of glacial acetic acid to obtain a yellow solution and zinc was added (100 eq.) causing immediate decolorization of the solution. After 5 min stirring at room temperature, TLC of the reaction mixture showed a nonpolar material. The acetic, acid was decanted and the solid washed with methylene chloride. The combined organic solutions were evaporated to obtain a crude solid which was redissolved in methylene chloride and washed with 2 or 3–50 mL portions of water. The crude material obtained after evaporation of methylene chloride was chromatographed on silica gel (20–30% ethyl acetate/hexane) to yield the pure product as a white solid.

The compounds 5a to 5j and intermediates were prepared as follows:

| Method | Compound 5 | Compound 4 | Zinc | Ethanol | NH$_4$Cl | Acetic Acid |
|---|---|---|---|---|---|---|
| A | a 0.10 g | a 0.65 g | 15 mL | 0.535 g | — | |
| B | b 0.20 g | b 1.30 g | — | — | 10 mL | |
| B | c 0.34 g | c 3.9 g | — | — | 10 mL | |
| B | d 0.12 g | d 1.4 g | — | — | 10 mL | |
| B | e 0.20 g | e 2.5 g | — | — | 10 mL | |
| B | f 0.080 g | f 0.4 g | — | — | 5 mL | |
| A | g 0.005 g | g 0.15 g | 10 mL | 0.15 g | — | |
| A | h 0.035 g | h 4.0 g | 15 mL | 4.0 g | — | |
| A | i 0.20 g | i 2.0 g | 20 mL | 2.0 g | — | |
| A | j 0.17 g | j 2.0 g | 50 mL | 2.0 g | — | |

Example 1

Synthesis of Compound 5a

2',6'-Difluorophenyl acridine-9-carboxylate (3a). Product was further purified by chromatography on silica gel (30% ethyl acetate/hexane) to yield the pure product as a creamy solid. $^1$H NMR (CDCl$_3$) δ 7.13–7.39 (m, 3H), 7.68–8.35 (m, 8H).

2',6'-Difluorophenyl 10-methylacridinium-9-carboxylate trifluoromethanesulfonate (4a). $^1$H NMR (acetone-d$_6$) δ 5.28 (s, 3H), 7.44–7.68 (m, 3H), 8.32–9.13 (m, 8H).

2',6'-Difluorophenyl 10-methylacridan-9-carboxylate (5a). Method A. $^1$H NMR (CDCl$_3$) δ 3.49 (s, 3H), 5.29 (s, 1H), 6.82–7.10 (m, 7 H) 7.29–7.41 (m, 4H).

Example 2

Synthesis of Compound 5b

3',5'-Difluorophenyl acridine-9-carboxylate (3b). $^1$H NMR (CDCl$_3$) δ 6.84–7.09 (m, 3H), 7.67–8.37 (m, 8H).

3',5'-Difluorophenyl 10-methylacridinium-9-carboxylate trifluoromethanesulfonate (4b). Compound 3b was reacted for three days with methyl trifluoromethanesulfonate in dichloromethane. $^1$H NMR (acetone-d$_6$) δ 5.25 (s, 3H), 7.22–7.59 (m, 3H), 8.23–9.09 (m, 8H).

3',5'-Difluorophenyl 10-methylacridan-9-carboxylate (5b). Method B. $^1$H NMR (CDCl$_3$) δ 3.44 (s, 3H), 5.16 (s, 1H), 6.49–6.65 (m, 3 H), 6.99–7.36 (m, 8H).

Example 3

Synthesis of Compound 5c

2',4',6'-Trichlorophenyl acridine-9-carboxylate (3c). Yellow solid: $^1$H NMR (CDCl$_3$) δ 7.55 (s, 2H) 7.67–8.61 (m, 8H).

2',4',6'-Trichlorophenyl 10-methylacridinium-9-carboxylate trifluoromethanesulfonate (4c). $^1$H NMR (acetone-d$_6$) δ 5.28 (s, 3H), 7.93 (s, 2H), 8.31–9.13 (m, 8H).

2',4',6'-Trichlorophenyl 10-methylacridan-9-carboxylate (5c). Method B. $^1$H NMR (CDCl$_3$) δ 3.42 (s, 3H), 5.27 (s, 1H), 6.97–7.39 (m, 10 H).

Example 4

Synthesis of Compound 5d

2',4',5'-Trichlorophenyl acridine-9-carboxylate (3d). Yellow solid: $^1$H NMR (CDCl$_3$) δ 7.63–8.34 (m, 10H).

2',4',5'-Trichlorophenyl 10-methylacridinium-9-carboxylate trifluoromethanesulfonate (4d). $^1$H NMR (acetone-d$_6$) δ 5.26 (s, 3H), 8.09 (s, 1H), 8.26–9.11 (m, 9H).

2',4',5'-Trichlorophenyl 10-methylacridan-9-carboxylate (5d). Method B. $^1$H NMR (CDCl$_3$) δ 3.43 (s, 3H), 5.23 (s, 1H), 6.97–7.42 (m, 10H).

Example 5

Synthesis of Compound 5e

2',3',6'-Trifluorophenyl acridine-9-carboxylate (3e). The yellow solid was further washed with ether to remove excess of phenol (82% yield): $^1$H NMR (CDCl$_3$) δ 7.08–7.28 (m, 2H) 7.71–8.42 (m, 8H).

2',3',6'-Trifluorophenyl 10-methylacridinium-9-carboxylate trifluoromethanesulfonate (4e). Due to low solubility, compound 3d was suspended in 25 mL of methylene chloride and treated according to the general procedure. $^1$H NMR (acetone-d$_6$) δ 5.29 (s, 3H), 7.50–7.67 (m, 2H), 8.26–9.14 (m, 8H).

2',3',6'-Trifluorophenyl 10-methylacridan-9-carboxylate (5e). Method B. $^1$H NMR (CDCl$_3$) δ 3.44 (s, 3H), 5.29 (s, 1H), 6.76–6.84 (m, 2 H) 6.99–7.39 (m, 8H).

Example 6

Synthesis of Compound 5f

Pentafluorofluorophenyl acridine-9-carboxylate (3f). $^1$H NMR (CDCl$_3$) δ 7.70–8.35 (m, 8H).

Pentafluorofluorophenyl 10-methylacridinium-9-carboxylate trifluoromethanesulfonate (4f). $^1$H NMR (acetone-d$_6$) δ 5.29 (s, 3H), 8.33–9.15 (m, 8H).

Pentafluorofluorophenyl 10-methylacridan-9-carboxylate (5f). Method B. $^1$H NMR (CDCl$_3$) δ 3.45 (s, 3H), 5.31 (s, 1H), 6.97–7.04 (m, 4 H), 7.32–7.37 (m, 4H).

Example 7

Synthesis of Compound 5g

2-Methoxyacridine-9-carboxylic acid (1 g). $^1$H NMR (DMSO-d$_6$) δ 3.967 (s, 3H), 7.22–8.30 (m, 7H).

2',3',6'-Trifluorophenyl 2-methoxyacridine-9-carboxylate (3 g). $^1$H NMR (CDCl$_3$) δ 4.030 ( s, 3H), 7.11–8.30 (m, 9H).

2',3',6'-Trifluorophenyl 2-methoxy-10-methylacridinium-9-carboxylate trifluoromethanesulfonate (4g). $^1$H NMR (DMSO-d$_6$) δ 4.113 (s, 3H), 4.974 (s, 3H), 7.57–8.97 (m, 9H).

2',3',6'-Trifluorophenyl 2-methoxy-10-methylacridan-9-carboxylate (5 g). Method A. $^1$H NMR (CDCl$_3$) δ 3.414 (s, 3H), 3.821 (s, 3H), 5.272 (s, 1H), 6.78–7.38 (m, 9H).

Example 8

Synthesis of Compound 5h.

3-Methoxyacridine-9-carboxylic acid (1 h). Condensation of the diarylamine with oxalyl chloride produced a mixture of the 3-methoxy and 1-methoxy isomers which were separated after conversion to the esters (3) by column chromatography on silica with 20% ethyl acetate/hexane. $^1$H NMR. (DMSO-d$_6$) δ 4.048 (s, 3H), 7.47–8.24 (m, 7H).

2',3',6'-Trifluorophenyl -methoxyacridine-9-carboxylate (3h).:$^1$H NMR (CDCl$_3$) δ 4.043 (s, 3H),7.08–8.25 (m, 9H).

2',3',6'-Trifluorophenyl 3-methoxy 10-methyl-acridinium-9-carboxylate trifluoromethanesulfonate (4h). $^1$H NMR (DMSO-d$_6$) δ 4.288 (s, 3H), 4.837 (s, 3H), 7.64–8.89 (m, 9H).

2',3',6'-Trifluorophenyl 3-methoxy-10-methylacridan-9-carboxylate (5h). Method A. $^1$H NMR (CDCl$_3$) δ 3.422 (s, 3H), 3.847 (s, 3H), 5.25 (s, 1H), 6.54–7.39 (m, 9H).

Example 9

Synthesis of Compound 5i

2',6'-Difluorophenyl 3-methoxyacridine-9-carboxylate (3i). A mixture of the 3-methoxy and 1-methoxy isomers was obtained which was separated by column chromatography on silica with 20% ethyl acetate/hexane. $^1$H NMR (CDCl$_3$) δ 4.047 (s, 3H),7.14–8.28 (m, 10H).

2',6'-Difluorophenyl 3-methoxy-10-methylacridinium-9-carboxylate trifluoromethanesulfonate (4i). $^1$H NMR (DMSO-d$_6$) δ 4.289 (s, 3H), 4.838 (s, 3H), 7.52–8.89 (m, 10H).

2',6'-Difluorophenyl 3-methoxy-10-methylacridan-9-carboxylate (5i). Method A. $^1$H NMR (CDCl$_3$) δ 3.416 (s, 3H), 3.843 (s, 3H), 5.241 (s, 1H), 6.53–7.39 (m, 10H).

Example 10

Synthesis of Compound 5j 2,7-Dimethoxyacridine-9-carboxylic acid (1j ). The acid was formed by the reaction sequence depicted in Scheme 2 with the exception that the condensation of the diarylamine with oxalyl chloride was performed in dichloromethane solvent. $^1$H NMR (DMSO-d$_6$) δ 3.862 (s, 6H), 7.234–7.242 (d, 2H), 7.523–7.583 (dd, 2H), 8.103–8.136 (d, 2H).

2',3',6'-Trifluorophenyl 2,7-dimethoxyacridine-9-carboxylate (3j). $^1$H NMR (CDCl$_3$) δ 4.010 (s, 6H), 7.06–7.25 (m, 2H), 7.379–7.387 (d, 2H), 7.436–7.476 (dd, 2H), 8.125–8.156 (d, 2H).

2',3',6'-Trifluorophenyl 2,7-dimethoxy-10-methylacridinium-9-carboxylate trifluoromethanesulfonate (4j). Compound 3i was reacted for several days with methyl trifluoromethanesulfonate in dichloromethane. The amine salt formed but did not crystallize from the reaction mixture. $^1$H NMR (acetone-d$_6$) δ 4.159 (s, 6H), 5.184 (s, 3H), 7.40–8.98 (m, 8H).

2',3',6'-Trifluorophenyl 2,7-dimethoxy-10-methylacridan-9-carboxylate (5j). Method A. $^1$H NMR (CDCl$_3$) δ 3.375 (s, 3H), 3.811 (s, 3H), 5.230 (s, 1H), 6.78–6.96 (m, 8H).

Comparative Example

4'-Fluorophenyl acridine-9-carboxylate. (90% yield): $^1$H NMR (CDCl$_3$) δ 7.21–7.47 (m, 4H), 7.67–8.39 (m, 8H). 4'-Fluorophenyl 10-methylacridinium-9-carboxylate trifluoromethanesulfonate). 4'-Fluorophenyl acridine-9-carboxylate was reacted for three days with methyl trifluoromethanesulfonate in dichloromethane. $^1$H NMR (acetone-d$_6$) δ 5.23 (s, 3H), 7.37–7.81 (m, 4H), 8.23–9.08 (m, 8H).

4'-Fluorophenyl 10-methylacridan-9-carboxylate. Method B. $^1$H NMR (CDCl$_3$) δ 3.43 (s, 3H), 5.17 (s, 1H), 6.84–7.38 (m, 12H).

Chemiluminescence Measurements

The experiments in the following examples were performed using either a Turner Designs TD-20e (Sunnyvale, Calif.) luminometer fitted with neutral density filter for light attenuation or a Labsystems Luminoskan (Helsinki, Finland) luminometer. Data collection, analysis and display were software controlled.

Example 11

Comparison of the Light Intensity-Time Profile for Detection of HRP with Compounds 5a–f, h, a Prior Art Acridan and Luminol. In separate experiments, 40 μL volumes of each of three formulations were reacted with 1 μL of a solution containing $1.4 \times 10^{-16}$ mol of HRP in water. The formulations consisted of: (1) 0.05 mM acridan compound 5a–f or h in 0.01M tris buffer, pH 8.0, 0.4 mM urea peroxide, 0.1 mM p-phenylphenol, 0.025% Tween 20, 1 mM EDTA; (2) an identical formulation containing the previously reported acridan 4'-fluorophenyl 10-methylacridan-9-carboxylate in place of the acridan 5a–f or h (F. McCapra, Pure Appl. Chem., 24, 611–629 (1970)) and (3) an optimized reagent containing luminol (Amersham ECL formulation and peroxide in separate bottles). FIGS. 1–7 show the improved generation of light emission using reagents containing acridans 5a–f and h of the present invention compared to the prior art reagents under these conditions.

Example 12

Optimization of Formulations. A matrix optimization experiment was done using acridans 5a, 5c, 5e and 5h (0.1 mM–0.05 mM) in solutions containing p-iodophenol (0.1–2.25 mM) or p-phenylphenol (0.01–2.25 mM), urea peroxide (0.1 mM–1 mM), Tween 20 (0–0.6%) in tris buffer, pH 8.0 (0.01–0.2M). Sensitivity and dynamic range were evaluated for detection of HRP in the range $1.4 \times 10^{-15}$ to $1.4 \times 10^{-19}$ mol of enzyme. An especially effective reagent consists of the acridan (0.05 mM), p-iodophenol (1.1 mM) or p-phenylphenol (0.1 mM), urea peroxide (0.4 mM), 1 mM EDTA, Tween 20 (0.025%) in tris buffer, pH 8.0 (0.01M). These conditions gave linear assays for HRP over the entire range of enzyme tested for each acridan compound. Light intensity is increased by the incorporation of CaCl$_2$ in the range 0.5–5 μM; higher levels cause background luminescence to increase.

Example 13

Figure 8:
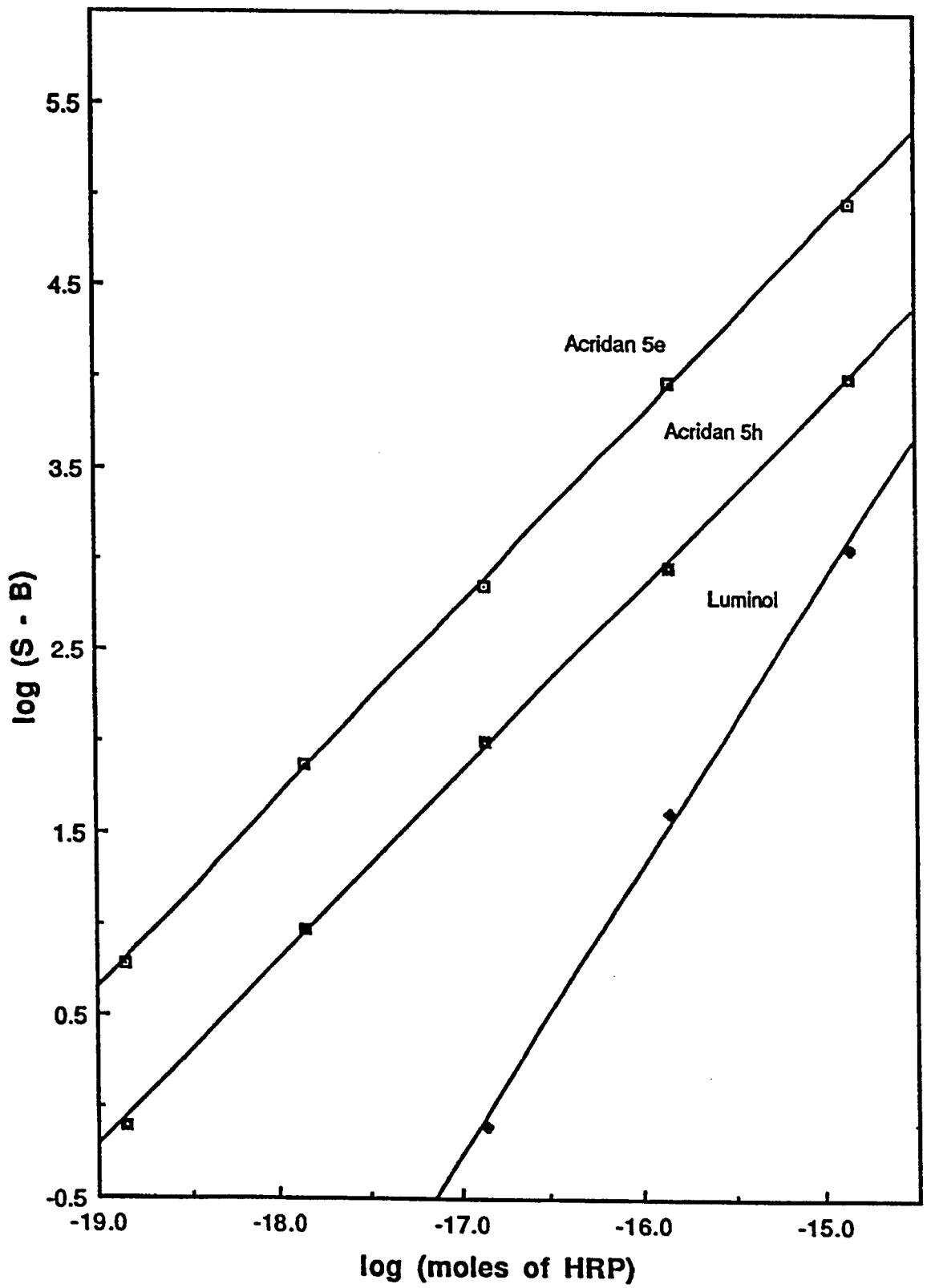
FIG. 8 is a graph showing a comparison of the linearity of detection of HRP using reagent compositions of the present invention and a commercially available optimized reagent containing luminol. In separate experiments, 40 μL of a solution containing acridan 5e, 5h or a commercial reagent (AMERSHAM ECL) were mixed at room temperature with 1 μL aliquots of HRP containing the indicated amounts of enzyme. Light intensities from the compositions containing acridans 5e and 5h were measured at 15 min while data from the ECL reagent represent the maximum light intensity. The term S-B refers to the chemiluminescence signal (S) in RLU in the presence of HRP corrected for background chemiluminescence (B) in the absence of HRP. Compositions containing acridans 5e and 5h are capable of 100-fold greater sensitivity of detection than the ECL reagent.

Comparison of the Sensitivity of Detection of HRP with 5e, 5h or Luminol. The linearity of detection of HRP using reagent compositions of the present invention and a commercially available optimized reagent containing luminol (Amersham ECL) were compared. Forty μL of a solution containing acridan 5e or 5h as described in example 2 and forty μL of the commercial reagent (Amersham ECL, prepared according to the manufacturer's directions) were mixed at room temperature with 1 μL aliquots of HRP containing between $1.4 \times 10^{-15}$ and $1.4 \times 10^{-19}$ mol of enzyme. FIG. 8 compares the linear range of HRP amount measured. Data from the reagents containing acridans 5e and 5h were measured at 15 min while data from the ECL reagent was measured at the point of maximum light intensity due to the faster rise and decay of light intensity for this reagent. However, the time to reach the maximum light intensity with the ECL reagent varies with the amount of HRP which makes measurement of the amount of HRP difficult. The term S-B refers to the chemiluminescence signal (S) in RLU in the presence of HRP corrected for background chemiluminescence (B) in the absence of HRP. Reagents containing acridans 5e and 5h are capable of 100-fold greater sensitivity of detection than the ECL reagent. Measurement with the reagents containing acridans 5e or 5h could be measured at earlier times with equivalent sensitivity.

Example 14

Stability of Horseradish Peroxidase Detection Reagent Containing 5e. The detection reagents are conveniently stored in two containers, the first comprising an aqueous buffer solution containing the peroxide, phenol enhancer, TWEEN 20 and EDTA, the second solution comprising the acridan compound 5 in a water-miscible organic solvent such as 1:1 ethanol/p-dioxane. When stored in this manner, the components are stable for several months. The final detection reagent is prepared by mixing appropriate quantities of the two solutions before use. An advantage of acridans of the present invention is their greater stability in the final detection reagent mixture. Stability is assessed by measuring the peak light intensity from an aliquot of the solution reacted with a specified amount of HRP. The peak light intensities ($I_{max}$) from 41 μL of a detection reagent containing compound 5e (0.05 mM), p-iodophenol (1.1 mM), urea peroxide (0.4 mM), TWEEN 20 (0.025%), EDTA (1 mM), 1.25% p-dioxane and 1.25% ethanol in 0.01M tris buffer, pH 8.0 reacted with $1.4 \times 10^{-16}$ mol of HRP at room temperature stored under various conditions are given below.

| Compound | Storage Time (hr) | Argon-Purged | $I_{max}$ (rel.) |
|---|---|---|---|
| 5e | 0 | no | 1.0 |
|  | 24 | no | 0.2 |
|  | 24 | yes | 1.0 |

Exclusion of oxygen from the detection reagent results in superior stability for 5e.

Example 15

Stability of Horseradish Peroxidase Detection Reagent Containing 5h. A similar set of experiments was performed using a reagent with the same composition containing instead acridan 5h. Stability was assessed by measuring the peak light intensity from an aliquot of the solution reacted with a specified amount of HRP. The peak light intensities ($I_{max}$) from 41 μL of a detection reagent containing compound 5h (0.05 mM), p-iodophenol (1.1 mM), urea peroxide (0.4 mM), TWEEN 20 (0.025%), EDTA (1 mM), 1.25% p-dioxane and 1.25% ethanol in 0.01M tris buffer, pH 8.0 reacted with $1.4 \times 10^{-16}$ mol of HRP at room temperature stored under various conditions are given below.

| Compound | Storage Time (hr) | Argon-Purged | $I_{max}$ (rel.) |
|---|---|---|---|
| 5h | 0 | no | 1.0 |
|  | 24 | no | 1.0* |
|  | 24 | yes | 1.0 |

A detection reagent incorporating acridan 5h shows superior stability compared to previous compounds and is stable for at least one day without special precautions.

* This solution showed a slower rise time to the peak light intensity.

Example 16

Effect of pH of the Buffer. Detection reagent solutions according to the composition of Example 14 were prepared with either 0.01M tris in the pH range 7.0–9.0 or 0.01M potassium phosphate in the pH range 6.0–6.5 and reacted with HRP. The best ratio of signal to reagent background resulted from reagents with a pH in the range 7.5–8.5.

Example 17

Effect of Buffer Salt. Detection reagent solutions according to the composition of example 14 were prepared with substitution of various buffer solutions and reacted with HRP. Useful levels of light intensity compared to reagent background were obtained with reagents prepared from tris hydrochloride, tris acetate, tris malate, potassium phosphate, diglycine-sodium hydroxide and tricine buffers.

Example 18

Effect of Enhancers. Detection reagent solutions according to the composition of example 14 were prepared with substitution of various phenolic enhancers and reacted with HRP. Useful levels of light intensity compared to reagent background were obtained with reagents incorporating p-iodophenol, p-hydroxycinnamic acid and p-phenylphenol.

Example 19

Effect of Peroxide. Detection reagent solutions according to the composition of example 14 were prepared with substitution of various peroxides and reacted with HRP. Useful levels of light intensity compared to reagent background were obtained with reagents incorporating hydrogen peroxide, sodium perborate and urea peroxide.

Example 20

Effect of Surfactant. Detection reagent solutions according to the composition of example 14 were prepared with substitution of various surfactants and reacted with HRP. Useful levels of light intensity compared to reagent background were obtained with reagents incorporating TWEEN (20 (Aldrich, Milwaukee, Wis.), TRITON (X-405 (Aldrich), BRIJ 35 (Aldrich), sodium dodecyl sulfate, cetyltrimethylammonium bromide, β-cyclodextrin and dextran sulfate.

Example 21

Improved Chemiluminescent Detection of Proteins by Western Blot

Rabbit anti-goat IgG-peroxidase conjugate was obtained from Cappel Products (Durham, N.C.). Human transferrin and fractionated goat anti-human transferrin serum were purchased from Sigma Chemical Co. (St. Louis, Mo.). The IgG sample was centrifuged at 10,000 g for two minutes and the supernatant was used in the immunological reaction. Polyvinylidene difluoride (PVDF) transfer membrane (IMMOBILON P) was obtained from Millipore Corp. (Bedford, Mass.). Kodak (Rochester, N.Y.) X-OMAT AR film was used in the assay procedure.

SDS-PAGE was performed utilizing the buffer system described by Laemmli (U. K. Laemmli, Nature (London), 227, 680 (1970)). The stacking gel was 4.38% acrylamide: 0.12% bisacrylamide. The separating gel was 6.81% acrylamide: 0.19% bisacrylamide. Following electrophoresis the gel was equilibrated for 7–8 minutes with the transfer buffer which contained 20 mM Tris, 153 mM glycine and 20% (v/v) methanol. The gel, sandwiched between a sheet of transfer membrane and a sheet of chromatography paper 3MM (Whatman), was placed in the transfer unit (Bio-Rad Laboratories, Richmond, Calif.). The proteins in the gel were electroeluted for 25 min at 4° C. at a 100 V constant voltage. The membrane was then placed in 50 mM Tris-HCl buffered saline at pH 7.4 (TBS) at 4° C. overnight. After this period the membrane was washed with TBS for 15 min.

The membrane was treated with 0.05% TWEEN-20 in 50 mM Tris-HCl buffered saline at pH 7.4 (T-TBS) containing 1% non-fat powdered milk (NFM) for one hour at room temperature. This blocked membrane was incubated for 75 minutes at room temperature with primary antibody (1:1500 dilution of goat anti-human transferrin IgG fraction) using T-TBS containing 1% NFM.

The membrane was then rinsed and washed three times for five min each with T-TBS at room temperature. The washed membrane was incubated for one hour at room temperature with secondary antibody (1:50,000 dilution of rabbit anti-goat IgG peroxidase conjugate) using T-TBS containing 1% NFM. The membrane was rinsed and washed four times for ten minutes each with T-TBS followed by a five min wash with TBS.

The washed membrane was soaked in one of four detection reagents for 5 min, drained and placed between sheets of transparency film. Reagent A was a commercial reagent containing luminol (Amersham ECL). Reagent B contained the acridan 4'-hydroxyphenyl 10-methylacridan-9-carboxylate previously disclosed in applicants' co-pending application Ser. No. 08/061,810. Reagent C contained acridan 5e. After an incubation period of 15 min, the X-ray film was exposed to the membrane for varying periods of time and developed. The composition of detection reagent solution containing the acridan compounds was:

| Tris buffer, pH 8.8 | 0.1 M |
|---|---|
| Acridan | 0.05 mM |
| p-iodophenol | 1.1 mM |
| TWEEN 20 | 0.5% (w/w) |
| $NaBO_3 \cdot 4H_2O$ | 2.5 mM |
| EDTA | 0.5 mM |
| p-Dioxane | 1.25% |
| Ethanol | 1.25% |

Figure 9A:
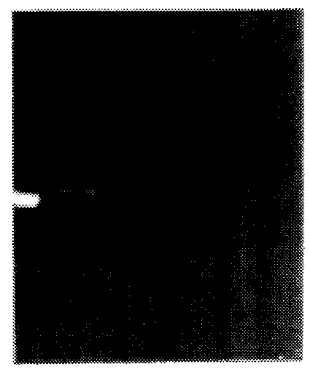
FIGS. 9A, 9B and 9C show the result of three experiments concerning Western blot analysis of human transferrin on PVDF with chemiluminescent detection using fractionated goat anti-human transferrin serum, rabbit anti-goat IgG-peroxidase conjugate. For each experiment, human transferrin loaded into the five slots was: (1) 1000 pg, (2) 200 pg, (3) 50 pg, (4) 20 pg, (5) 5 pg. Chemiluminescent detection was performed using: a commercial reagent (ECL) containing luminol (FIG. 9A); a reagent composition containing the acridan 4'-hydroxyphenyl 10-methylacridan-9-carboxylate previously disclosed in applicants' co-pending application Ser. No. 08/061,810 (FIG. 9B); and a reagent composition containing the acridan 5e of the present invention (FIG. 9C). The blots were exposed to X-OMAT AR X-ray film for 15 sec after a 14 minute incubation. The image has been scanned and digitally reproduced. The results show the superior image obtained with acridan 5e of the present invention.
Figure 9B:
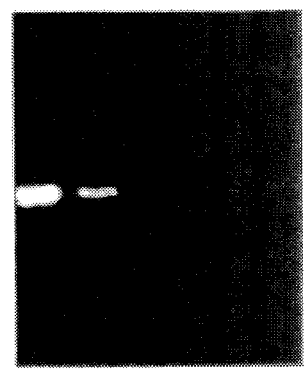
Figure 9C:
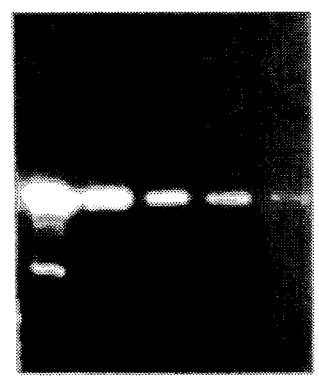

The transferrin standards utilized were clearly visible down to 5 pg/slot over the background after a 15 s exposure to Kodak X-OMATARX-ray film. It was possible to make several exposures of the membrane during a period of 24 hours as the membrane continued to emit light. FIG. 9 is a digitally scanned image of the X-ray film record of an experiment using a 14 min incubation and 15 s exposure.

Example 22

Figure 10A:
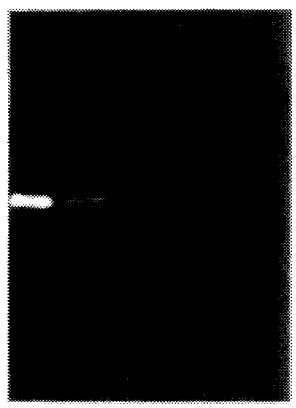
FIGS. 10A, 10B and 10C show the result of a Western blot analysis of human transferrin on nitrocellulose with chemiluminescent detection using fractionated goat anti-human transferrin serum, rabbit anti-goat IgG-peroxidase conjugate. Human transferrin loaded into each slot was (1) 1000 pg, (2) 200 pg, (3) 50 pg, (4) 20 pg, (5) 5 pg. Chemiluminescent detection was performed using: a commercial reagent (ECL) containing luminol (FIG. 10A); a reagent composition containing the acridan 4'-hydroxyphenyl 10-methylacridan-9-carboxylate previously disclosed in applicants' co-pending application Ser. No. 08/061,810 (FIG. 10B); and a reagent composition containing the acridan 5e of the present invention (FIG. 10C). The blots were exposed to X-OMAT AR X-ray film for one minute after a 15 minute incubation. The image has been scanned and digitally reproduced. The results show the superior image obtained with acridan 5e of the present invention.
Figure 10B:
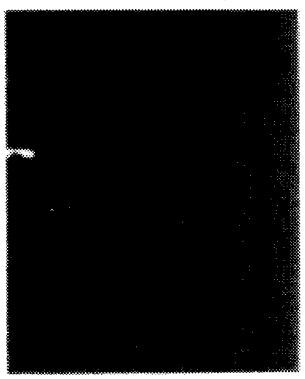
Figure 10C:
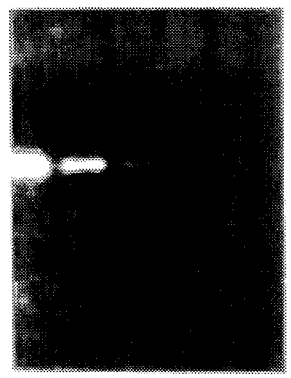

Chemiluminescent Detection of Proteins by Western Blot using Nitrocellulose Membrane. A Western blot analysis of human transferrin was conducted by the method of example 21 with blotting of protein onto nitrocellulose in place of PVDF. The transferrin standards utilized were clearly visible down to 20 pg/slot over the background after a one min exposure to Kodak X-OMAT AR X-ray film. It was possible to make several exposures of the membrane over a period of 12 hours as the membrane continued to emit light. FIG. 10 is a digitally scanned image of the X-ray film record of an experiment using a 15 min incubation and 1 min exposure.

Example 23

Figure 11:
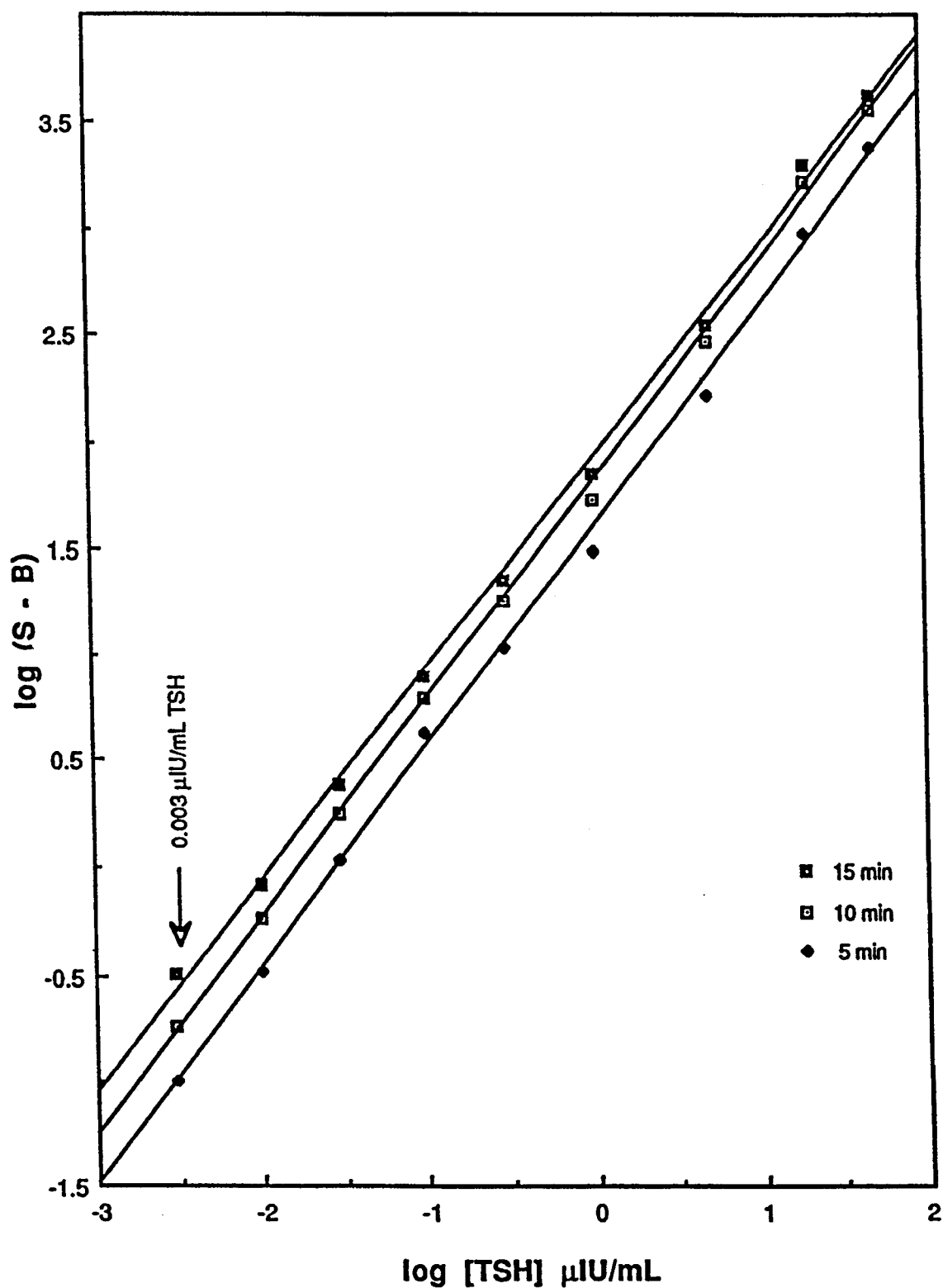
FIG. 11 is a graph showing the linearity of detection of thyroid stimulating hormone (TSH) in a chemiluminescent enzyme immunoassay using a reagent of the present invention containing acridan 5h and a commercial TSH immunoassay kit. The chemiluminescent assay resulted in a linear calibration curve over four orders of magnitude with a lowest detected quantity of 0.003 mIU/L. Excellent linearity and identical analytical sensitivity resulted when light intensity was measured at either 5, 10 or 15 min in each well. The term S-B has the same meaning as in FIG. 8. For comparison, the detection limit of the manufacturer's assay using a colorimetric endpoint is 0.05 mIU/L.

TSH Enzyme Immunoassay A TSH assay was performed using the components of a COBAS Core enzyme immunoassay kit for TSH from Roche (Basel, Switzerland) and a detection reagent of the present invention. The detection reagent comprised:

| Tris buffer, pH 8.0 | 0.01 M |
|---|---|
| Acridan 5h | 0.05 mM |
| p-iodophenol | 1.1 mM |
| TWEEN 20 | 0.025% (w/w) |
| Urea peroxide | 0.4 mM |
| EDTA | 1 mM |
| p-Dioxane | 1.25% |
| Ethanol | 1.25% | and could be prepared up to one day in advance. Samples prepared from the supplied standards were treated according to the manufacturer's instructions up to the detection stage. At this point, beads coated with the primary antibody/TSH/ secondary antibody-HRP immunological complex were treated with 100 μL of detection reagent in wells of a white 96 well plate (Dynatech Microlite 1). Chemiluminescence intensities were measured in a Labsystems Luminoskan luminometer every 2.5 min. The assay resulted in a linear calibration curve over four orders of magnitude with a lowest detected quantity of 0.003 mIU/L. Excellent linearity and identical analytical sensitivity resulted when light intensity was measured at 5, 10 or 15 min in each well (FIG. 11). The term S-B refers to the chemiluminescence signal (S) in RLU in the presence of HRP corrected for background chemiluminescence (B) in the absence of HRP. The quoted analytical sensitivity of the manufacturer's assay which uses a colorimetric endpoint is 0.05 mIU/L.

Example 24

Figure 12:
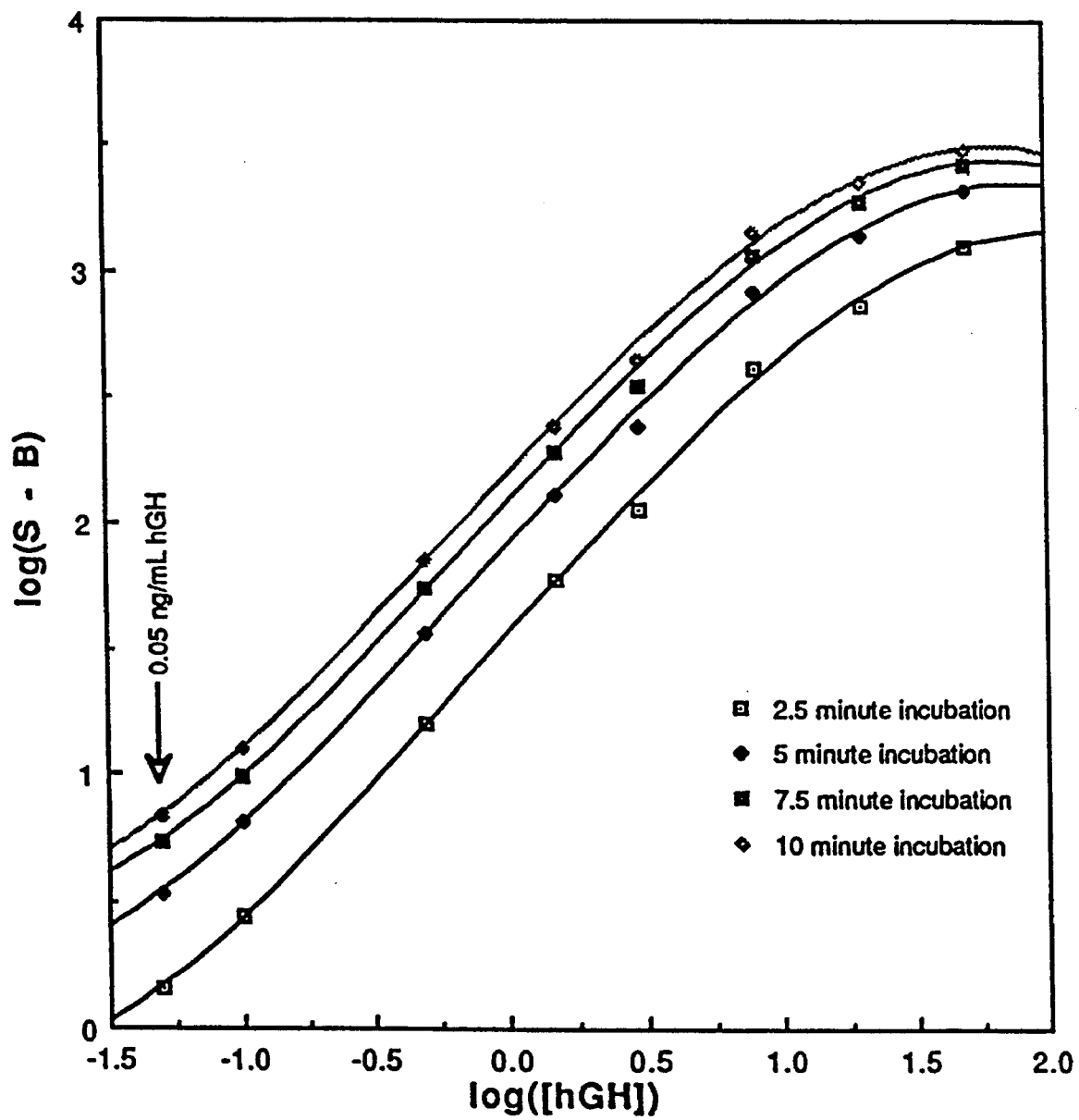
FIG. 12 is a graph showing the application of a chemiluminescent reagent of the invention containing acridan 5h in an enzyme immunoassay of FIG. 11 for human growth hormone (hGH). A commercially available colorimetric assay kit from Sorin Biomedica (Vercelli, Italy) was used according to the kit instructions with substitution of the detection reagent. The chemiluminescent assay resulted in a nonlinear calibration curve. The term S-B has the same meaning as in FIG. 8.

Human Growth Hormone Enzyme Immunoassay An hGH assay was performed using the components of a sandwich enzyme immunoassay kit for hGH from Sorin Biomedica (Vercelli, Italy) and a detection reagent of the present invention. The detection reagent comprised:

| Tris buffer, pH 8.0 | 0.01 M |
|---|---|
| Acridan 5h | 0.05 mM |
| p-iodophenol | 1.1 mM |
| Tween 20 | 0.025% (w/w) |
| Urea peroxide | 0.4 mM |
| EDTA | 1 mM |
| p-Dioxane | 1.25% |
| Ethanol | 1.25% | and could be prepared up to one day in advance. Samples prepared from the supplied standards were treated according to the manufacturer's instructions up to the detection stage. Upon completing the immunological reaction, the streptavidin-coated wells (supplied by the manufacturer) with bound biotin-primary antibody/TSH/secondary antibody- HRP immunological complex were treated with 100 μL of detection reagent. Chemiluminescence intensities were measured in a Labsystems Luminoskan luminometer every 2.5 min. A nonlinear calibration curve resulted which allowed direct measurement of hGH down to 0.05 ng/mL (FIG. 12). The term S-B refers to the chemiluminescence signal (S) in RLU in the presence of HRP corrected for background chemiluminescence (B) in the absence of HRP.

Figure 13:
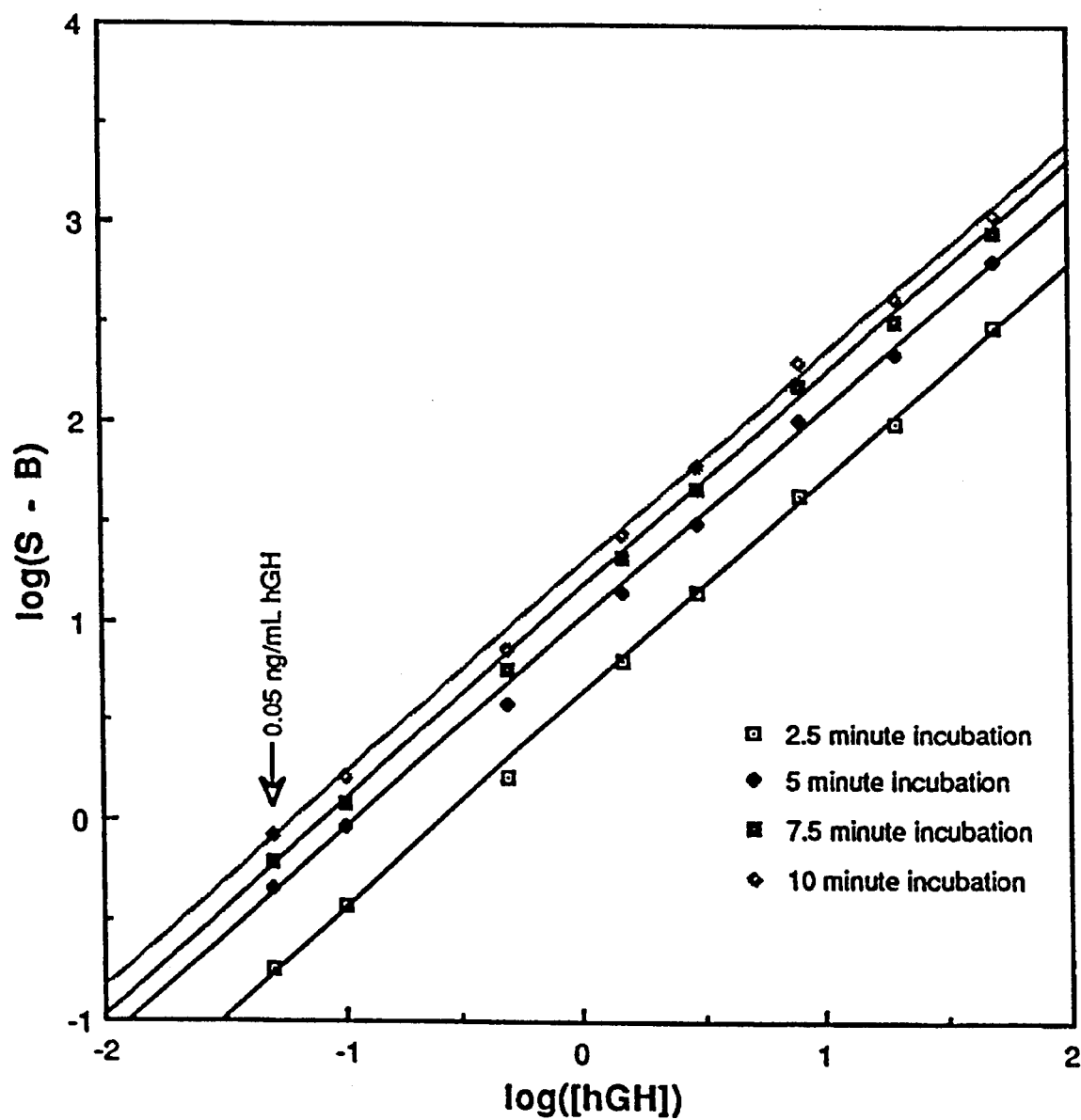
FIG. 13 is a graph showing the linearity of detection of hGH obtained in the same chemiluminescent enzyme immunoassay by diluting the secondary antibody-HRP conjugate ten-fold. The chemiluminescent assay resulted in a linear calibration curve over three orders of magnitude with a lowest detected quantity of 0.05 ng/mL. Excellent linearity and identical analytical sensitivity resulted when light intensity was measured at either 2.5, 5, 7.5 or 10 min. The term S-B has the same meaning as in FIG. 8. For comparison, the calculated detection limit of the manufacturer's assay using a colorimetric endpoint is 0.05 ng/mL; the colorimetric assay generates a nonlinear calibration curve.

The assay was repeated with a modification in which the secondary antibody-HRP conjugate supplied in the kit was diluted 10-fold with a dilution buffer supplied by the manufacturer. The assay resulted in a linear calibration curve over three orders of magnitude with a demonstrated detection limit of 0.05 ng/mL of hGH. Excellent linearity and identical analytical sensitivity resulted when light intensity was measured at 2.5, 5, 7.5 or 10 min (FIG. 13). Calibration data supplied by the manufacturer for the colorimetric method results in a nonlinear curve covering two orders of magnitude and requires a 30 min detection time. The calculated analytical sensitivity (signal>2 standard deviations of blank) of the manufacturer's assay is 0.05 ng/mL.

Example 25

Chemiluminescent Detection of Southern Blots. Mouse genomic DNA (Clontech Laboratories. Inc., Palo Alto, Calif.) was cleaved to completion with restriction endonuclease EcoR1 (Boehringer-Mannheim) at a concentration of 50 μg/mL. The restricted DNA was purified by extraction once with phenol/chloroform, once with chloroform and was precipitated with ethanol. The purified DNA was divided into two portions containing 30 and 15 μg of DNA, respectively and was separated by 0.77% agarose gel electrophoresis. The electrophoresis buffer was 40 mM Tris-acetate and 2 mM EDTA (pH 8.0). After electrophoresis the gel was rinsed with $H_2O$ and then soaked in 0.25N HCl for 12 min with gentle agitation.

MAGNAGRAPH NYLON (Micron Separations Inc., Westboro, Mass.) was soaked sequentially in water and 10X SSC (20X SSC is 3M NaCl, 0.3M sodium citrate, pH 7.0) for 2 and 10 min, respectively. The gel was rinsed with water and then treated with 0.5M NaOH/1.5M NaCl twice for 15 and 30 minutes, respectively. The gel was rinsed with water and then treated with 1M Tris-HCl (pH 7.5)/1.5M NaCl three times for 15 min each. The DNA in the gel was transferred onto the membrane by capillary blotting overnight using 10X SSC. The blots were air-dried for 30 min followed by baking at 80° C. for 2 hours.

The membranes were prehybridized in hybridization buffer (Amersham #RPN.3000) containing 0.5 NaCl and 5% blocking agent (Amersham #RPN.3000) for 60 minutes at 42° C. with occasional agitation. The hybridization probe, v-mos DNA (Clontech Lab. Inc.) was labeled with HRP according to the manufacturer's instructions (Amersham #RPN.3000) and the hybridization proceeded overnight at 42° C. using a hybridization buffer containing 0.5N NaCl, 5% blocking agent, and 300 ng/mL HRP-labeled v-mos DNA. The membranes were washed sequentially with room temperature 0.5X SSC/0.4% SDS for 5 and 30 min, then again at 55° C. three times for 15 min each, followed by two washes with 2X SSC for 5 min each at room temperature.

The membranes were rinsed with water and placed on 3MM blotting paper for one minute to remove excess solution, then transferred to a clean container followed by the addition of the detection reagent of Example 21. After a one minute incubation, excess solution was drained off and the blots were placed between sheets of transparency film followed by exposure to Kodak X-OMAT XAR 5 film.

Figure 14A:
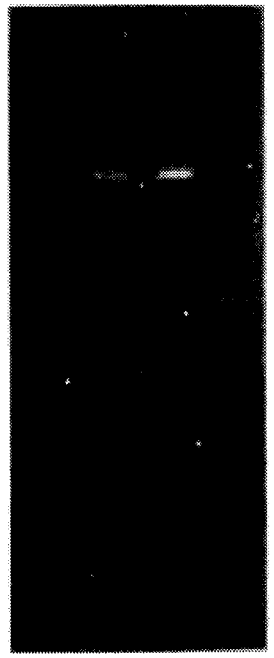
FIGS. 14A and 14B show the result of chemiluminescent detection of a Southern blot analysis of EcoRI-restricted mouse genomic DNA on nylon using a fluorescein-labeled v-mos probe and horseradish peroxidase-anti-fluorescein conjugate. In separate experiments, the reagents used for the chemiluminescent detection were: a composition of the present invention containing acridan 5e (FIG. 14A) and a commercial reagent (ECL) containing luminol (FIG. 14B). The blots were exposed to X-OMAT AR X-ray film for 10 min after a 22 min incubation. The image has been scanned and digitally reproduced. The results show the superior image obtained with acridan 5e of the present invention.
Figure 14B:
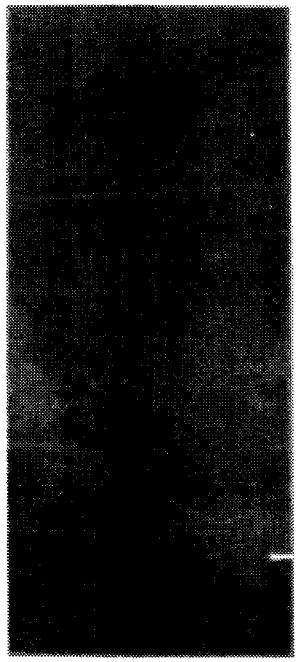

The reagent of the present invention can be used to detect a single copy gene in mouse genomic DNA as shown in FIG. 14A. The target restriction fragment is 14 kb providing 70 pg ($7 \times 10^{-17}$ moles) of target DNA in the 15 μg leading tracks. The single copy gene was clearly visible in both tracks of the blot using the detection reagent of the present invention (FIG. 14A) while the luminol reagent did not permit the bands to be detected (FIG. 14B).

It is intended that the foregoing description be only illustrative of the present invention and that the present invention be limited only by the appended claims.

We claim:

1. A method for producing chemiluminescence which comprises reacting a peroxide and a peroxidase with an acridan of the formula:

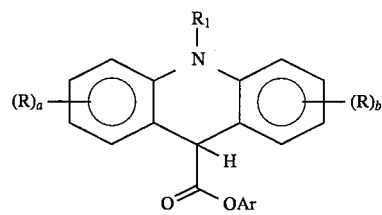

wherein $R_1$ is selected from the group consisting of alkyl, heteroalkyl and aralkyl groups, wherein R is a group which allows production of chemiluminescence and a and b are integers between 0 and 4 and wherein OAr is a leaving group selected from the group consisting of di- and polyhalosubstituted phenoxy groups, which leaving group allows the production of chemiluminescence from the acridan by reaction with the peroxide and the peroxidase.

2. The method of claim 1 wherein OAr is a polyhalosubstituted phenoxy group.

3. The method of claim 1 wherein the di- or polyhalo-substituted phenoxy group is represented by the formula $OC_6H_{5-m}X_m$ wherein X is a halogen atom selected from F and Cl, and m is 2 to 5.

4. The method of any one of claims 1, 2 or 3 wherein at least one R group is an alkoxy group and the remaining of the R groups are hydrogen.

5. The method of any one of claims 1, 2 or 3 wherein at least one R group is a methoxy group and the remaining of the R groups are hydrogen.

6. A reagent composition which generates chemiluminescence in the presence of a peroxidase, which comprises:

(a) an acridan of the formula:

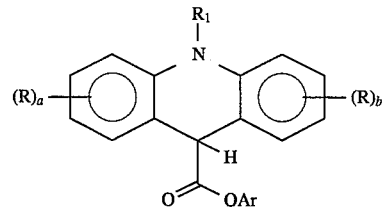

wherein $R_1$ is selected from the group consisting of alkyl, heteroalkyl and aralkyl groups, wherein R is a group which allows production of chemiluminescence and a and b are integers between 0 and 4 and wherein OAr is a leaving group selected from the group consisting of di- and polyhalosubstituted phenoxy groups, which leaving group allows the production of chemiluminescence from the acridan by reaction with a peroxide and the peroxidase;

(b) the peroxide in an amount which induces the reaction of the acridan with the peroxidase;

(c) a chelating agent in an amount which prevents the peroxide from reacting prior to addition of the peroxidase to the composition; and (d) a surfactant in an amount which provides for improved chemiluminescence.

7. The composition of claim 6 further comprising a phenolic compound in an amount which enhances chemiluminescence production from the acridan.

8. The composition of claim 6 wherein OAr is a polyhalosubstituted phenoxy group.

9. The composition of claim 6 wherein the di- or polyhalosubstituted phenoxy group is represented by the formula $OC_6H_{5-m}X_m$ wherein X is a halogen atom selected from F and Cl, and m is 2 to 5.

10. The composition of any one of claims 6, 8, or 9 wherein at least one R group is an alkoxy group and the remaining of the R groups are hydrogen.

11. The composition of any of claims 6, 8 or 9 wherein at least one R group is a methoxy group and the remaining of the R groups are hydrogen.

12. A method for detecting an analyte selected from the group consisting of peroxidase alone, organic molecules labeled with the peroxidase and biological molecules labeled with the peroxidase in an assay procedure by a chemiluminescent reaction which comprises:

(a) providing a reagent composition which generates chemiluminescence in the presence of the peroxidase, said reagent composition comprising an acridan of the formula

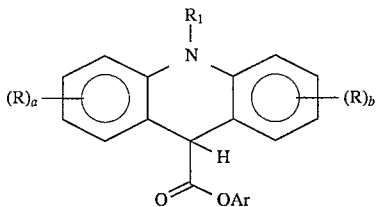

wherein $R_1$ is selected from the group consisting of alkyl, heteroalkyl and aralkyl groups, wherein R is a group which allows production of chemiluminescence and a and b are integers between 0 and 4 and wherein OAr is a leaving group selected from the group consisting of di- and polyhalosubstituted phenoxy groups, which leaving group allows the production of chemiluminescence from the acridan by reaction with a peroxide and the peroxidase; the peroxide in an amount which induces the reaction of the acridan with the peroxidase; a chelating agent in an amount which prevents the peroxide from reacting prior to addition of the peroxidase to the composition; and a surfactant in an amount which provides improved chemiluminescence; and (b) reacting the peroxidase with the reagent composition so that chemiluminescence is produced to thereby detect the analyte.

13. The method of claim 12 further comprising including a phenolic compound in the reagent composition in an amount which enhances chemiluminescence production from the acridan in the reagent composition.

14. The method of claim 12 wherein OAr is a polyhalosubstituted phenoxy group.

15. The method of claim 12 wherein the di- or polyhalosubstituted phenoxy group is represented by the formula $OC_6H_{5-m}X_m$ wherein X is a halogen atom selected from F and Cl, and m is 2 to 5.

16. The method of any of claims 12, 14, or 15 wherein at least one R group is an alkoxy group and the remaining of the R groups are hydrogen.

17. The method of any of claims 12, 14 or 15 wherein at least one R group is a methoxy group and the remaining of the R groups are hydrogen.

18. A method of detecting an analyte selected from the group consisting of hydrogen peroxide, hydrogen peroxide generated by an enzyme, peroxidase alone, organic molecules labeled with the peroxidase and biological molecules labeled with the peroxidase in an assay procedure by a chemiluminescent reaction which comprises:

(a) reacting an acridan with a peroxide and the peroxidase, wherein the acridan is of the formula:

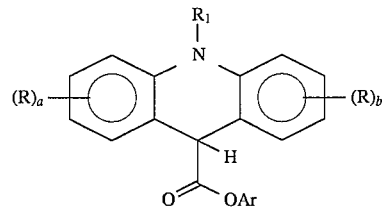

wherein $R_1$ is selected from the group consisting of alkyl, heteroalkyl and aralkyl groups, wherein R is a group which allows production of chemiluminescence and a and b are integers between 0 and 4 and wherein OAr is a leaving group selected from the group consisting of di- and polyhalosubstituted phenoxy groups, which leaving group allows the production of chemiluminescence from the acridan by reaction with the peroxide and the peroxidase; and (b) detecting the chemiluminescence to thereby detect the analyte.

19. The method of claim 18 wherein OAr is a polyhalosubstituted phenoxy group.

20. The method of claim 18 wherein the di- or polyhalosubstituted phenoxy group is represented by the formula $OC_6H_{5-m}X_m$ wherein X is a halogen atom selected from F and Cl, and m is 2 to 5.

21. The method of any of claims 18, 19, or 20 wherein at least one R group is an alkoxy group and the remaining of the R groups are hydrogen.

22. The method of any of claims 18, 19 or 20 wherein at least one R group is a methoxy group and the remaining of the R groups are hydrogen.

23. A method of detecting a peroxidase in an assay procedure by a chemiluminescent reaction which comprises:

(a) reacting the peroxidase in the presence of a peroxide and an acridan of the formula:

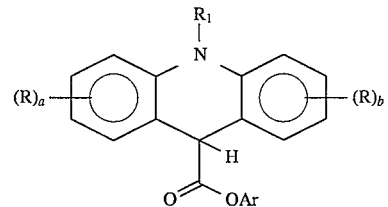

wherein $R_1$ is selected from the group consisting of alkyl, heteroalkyl and aralkyl groups, wherein R is a group which allows production of chemiluminescence and a and b are integers between 0 and 4 and wherein OAr is a leaving group selected from the group consisting of di- and polyhalosubstituted phenoxy groups, which leaving group allows the production of chemiluminescence from the acridan by reaction with the peroxide and the peroxidase; and (b) detecting the chemiluminescence to thereby detect the peroxidase.

24. The method of claim 23 wherein OAr is a polyhalosubstituted phenoxy group.

25. The method of claim 23 wherein the polyhalosubstituted phenoxy group is represented by the formula $OC_6H_{5-m}X_m$ wherein X is a halogen atom selected from F and Cl, and m is 2 to 5.

26. The method of any of claims 23, 24 or 25 wherein at least one R group is an alkoxy group and the remaining of the R groups are hydrogen.

27. The method of any of claims 23, 24 or 25 wherein at least one R group is a methoxy group and the remaining of the R groups are hydrogen.

28. A kit for detecting in a sample an analyte selected from the group consisting of hydrogen peroxide, hydrogen peroxide generated by an enzyme, peroxidase alone, organic molecules labeled with the peroxidase and biological molecules labeled with the peroxidase in an assay procedure by a chemiluminescent reaction which comprises in separate containers:

(a) an acridan of the formula

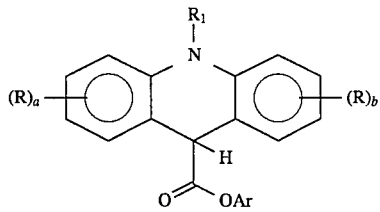

wherein $R_1$ is selected from the group consisting of alkyl, heteroalkyl and aralkyl groups, wherein R is a group which allows production of chemiluminescence and a and b are integers between 0 and 4 and wherein O—Ar is a leaving group selected from the group consisting of di- and polyhalosubstituted phenoxy groups, which leaving group allows the production of chemiluminescence from the acridan by reaction with a peroxide and the peroxidase; and (b) one member selected from the group consisting of a peroxide and a peroxidase enzyme either singly or attached to an analyte-binding compound, wherein the chemiluminescence is detected in the assay procedure by reacting the acridan with the peroxide and the peroxidase to thereby detect the analyte in the sample.

29. The kit of claim 28 wherein OAr is a polyhalosubstituted phenoxy group.

30. The kit of claim 28 wherein the polyhalosubstituted phenoxy group is represented by the formula $OC_6H_{5-m}X_m$ wherein X is a halogen atom selected from F and Cl, and m is 2 to 5.

31. The kit of any of claims 28, 29 or 30 wherein at least one R group is an alkoxy group and the remaining of the R groups are hydrogen.

32. The kit of any of claims 28, 29 or 30 wherein at least one R group is a methoxy group and the remaining of the R groups are hydrogen.

33. A kit for detecting in a sample an analyte selected from the group consisting of peroxidase alone, organic molecules labeled with the peroxidase and biological molecules labeled with the peroxidase in an assay procedure by a chemiluminescent reaction which comprises in separate containers:

(a) a reagent composition which generates light in the presence of the peroxidase, said reagent composition comprising an acridan of the formula:

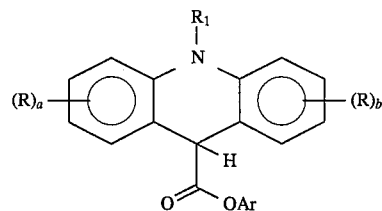

wherein $R_1$ is selected from the group consisting of alkyl, heteroalkyl and aralkyl groups, wherein R is a group which allows production of chemiluminescence and a and b are integers between 0 and 4 and wherein OAr is a leaving group selected from the group consisting of di- and polyhalosubstituted phenoxy groups, which leaving group allows the production of chemiluminescence from the acridan by reaction with a peroxide and a peroxidase; a peroxide in an amount which induces the reaction of the acridan with the peroxidase; a chelating agent in an amount which prevents the peroxide from reacting prior to addition of the peroxidase to the composition; and a surfactant in an amount which provides improved chemiluminescence; and (b) the peroxidase either singly or attached to an analyte-binding compound, wherein the chemiluminescence is detected in the assay procedure by reacting the reagent composition with the peroxidase to thereby detect the analyte in the sample.

34. The kit of claim 33 further comprising including a phenolic compound in the reagent composition in an amount which enhances chemiluminescence production from the acridan in the reagent composition.

35. The kit of claim 33 wherein OAr is a polyhalosubstituted phenoxy group.

36. The kit of claim 33 wherein the polyhalosubstituted phenoxy group is represented by the formula $OC_6H_{5-m}X_m$ wherein X is a halogen atom selected from F and Cl, and m is 2 to 5.

37. The kit of any of claims 33, 35 or 36 wherein at least one R group is an alkoxy group and the remaining of the R groups are hydrogen.

38. The kit of any of claims 33, 35 or 36 wherein at least one R group is a methoxy group and the remaining of the R groups are hydrogen.

* * * * *